(12) United States Patent
Beauchemin

(10) Patent No.: US 9,970,984 B2
(45) Date of Patent: May 15, 2018

(54) METHOD AND APPARATUS FOR IDENTIFYING DEFECTS IN A CHEMICAL SENSOR ARRAY

(71) Applicant: Life Technologies Corporation, Carlsbad, CA (US)

(72) Inventor: Mark Beauchemin, S. Glastonbury, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days. days.

(21) Appl. No.: 13/690,959

(22) Filed: Nov. 30, 2012

(65) Prior Publication Data

US 2013/0143221 A1 Jun. 6, 2013

Related U.S. Application Data

(60) Provisional application No. 61/565,602, filed on Dec. 1, 2011.

(51) Int. Cl.
| | | |
|---|---|---|
| *G01R 31/30* | (2006.01) | |
| *G01R 31/327* | (2006.01) | |
| *G01R 31/28* | (2006.01) | |
| *G01N 27/414* | (2006.01) | |
| *G01N 27/416* | (2006.01) | |
| *G01R 31/26* | (2014.01) | |

(52) U.S. Cl.
CPC ....... *G01R 31/2851* (2013.01); *G01N 27/414* (2013.01); *G01N 27/416* (2013.01); *G01N 27/4145* (2013.01); *G01R 31/2621* (2013.01)

(58) Field of Classification Search
CPC ............. G01N 27/416; G01N 27/4145; G01R 31/2851; G01R 31/2621
See application file for complete search history.

(56) References Cited

U.S. PATENT DOCUMENTS

| | | |
|---|---|---|
| 4,086,642 A | 4/1978 | Yoshida et al. |
| 4,411,741 A | 10/1983 | Janata |
| | (Continued) | |

FOREIGN PATENT DOCUMENTS

| | | |
|---|---|---|
| CN | 1582334 | 2/2005 |
| CN | 1585896 | 2/2005 |
| | (Continued) | |

OTHER PUBLICATIONS

Sakata, Toshiya, and Yuji Miyahara. "Direct Detection of Single-Base Extension Reaction Using Genetic Field Effect Transistor." Microtechnology in Medicine and Biology, 2005. 3rd IEEE/EMBS Special Topic Conference on. IEEE, 2005.*

(Continued)

*Primary Examiner* — Robert Eom

(57) ABSTRACT

In one implementation, a method for operating an apparatus is described. The method includes applying a bias voltage to place a transistor of a reference sensor in a known state. The reference sensor is in an array of sensors that further includes a chemical sensor coupled to a reaction region for receiving at least one reactant. The method further includes acquiring an output signal from the reference sensor in response to the applied bias voltage. The method further includes determining a defect associated with the array if the output signal does not correspond to the known state.

5 Claims, 6 Drawing Sheets

(56) References Cited

U.S. PATENT DOCUMENTS

| | | | |
|---|---|---|---|
| 4,437,969 A | 3/1984 | Covington et al. |
| 4,438,354 A | 3/1984 | Haque et al. |
| 4,444,644 A | 4/1984 | Hiramoto |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Ligtenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,126,759 A | 6/1992 | Small et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi et al. |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kinlger et al. |
| 6,613,513 B1 | 9/2003 | Parce et al. |
| 6,618,083 B1 | 9/2003 | Chen et al. |
| 6,624,637 B1 | 9/2003 | Pechstein et al. |
| 6,627,154 B1 | 9/2003 | Goodman et al. |
| 6,654,505 B2 | 11/2003 | Bridgham et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,780,591 B2 | 8/2004 | Williams et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,929,944 B2 | 8/2005 | Matson |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2* | 3/2006 | Eversmann et al. ..... 250/370.14 |
| 7,022,288 B1 | 4/2006 | Boss |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakov et al. |
| 7,087,387 B2 | 8/2006 | Gerdes et al. |
| 7,090,975 B2 | 8/2006 | Shultz et al. |
| 7,091,059 B2 | 8/2006 | Rhodes |
| 7,097,973 B1 | 8/2006 | Zenhausern |
| 7,105,300 B2 | 9/2006 | Parce et al. |
| 7,106,089 B2 | 9/2006 | Nakano et al. |
| 7,169,560 B2 | 1/2007 | Lapidus et al. |
| 7,173,445 B2 | 2/2007 | Fujii et al. |
| 7,190,026 B2 | 3/2007 | Lotfi et al. |
| 7,192,745 B2 | 3/2007 | Jaeger |

(56) References Cited

U.S. PATENT DOCUMENTS

| | | |
|---|---|---|
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |
| 7,235,389 B2 | 6/2007 | Lim et al. |
| 7,238,323 B2 | 7/2007 | Knapp et al. |
| 7,239,188 B1 | 7/2007 | Xu et al. |
| 7,244,559 B2 | 7/2007 | Rothberg et al. |
| 7,244,567 B2 | 7/2007 | Chen |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,575,865 B2 | 8/2009 | Leamon et al. |
| 7,576,037 B2 | 8/2009 | Engelhardt et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,817 B2 | 11/2009 | Tay |
| 7,614,135 B2 | 11/2009 | Santini, Jr. et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,785,790 B1 | 8/2010 | Church et al. |
| 7,824,900 B2 | 11/2010 | Iwadate et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,885,490 B2 | 2/2011 | Heideman et al. |
| 7,888,013 B2 | 2/2011 | Miyahara et al. |
| 7,888,708 B2 | 2/2011 | Yazawa et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,067,731 B2 | 11/2011 | Matyjaszczyk et al. |
| 8,072,188 B2 | 12/2011 | Yorinobu et al. |
| 8,133,698 B2 | 3/2012 | Silver |
| 8,138,496 B2 | 3/2012 | Li et al. |
| 8,154,480 B2 | 4/2012 | Shishido et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,813 B2 | 7/2012 | Burdett et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,415,716 B2 | 4/2013 | Rothberg et al. |
| 8,421,437 B2 | 4/2013 | Levine |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,487,790 B2 | 7/2013 | Fife et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick et al. |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |
| 8,685,298 B2 | 4/2014 | Rockenschaub et al. |
| 8,728,844 B1 | 5/2014 | Liu et al. |
| 8,731,847 B2 | 5/2014 | Johnson et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,841,217 B1 | 9/2014 | Fife et al. |
| 8,847,637 B1 | 9/2014 | Guyton |
| 8,912,005 B1 | 12/2014 | Fife et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,164,070 B2 | 10/2015 | Fife |
| 9,201,041 B2 | 12/2015 | Dalton et al. |
| 9,270,264 B2 | 2/2016 | Jordan et al. |
| 9,389,199 B2 | 7/2016 | Cheng et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0012937 A1 | 1/2002 | Tender et al. |
| 2002/0029971 A1 | 3/2002 | Kovacs |

(56) References Cited

U.S. PATENT DOCUMENTS

| | | |
|---|---|---|
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0061529 A1 | 5/2002 | Bridgham et al. |
| 2002/0081714 A1 | 6/2002 | Jain et al. |
| 2002/0085136 A1 | 7/2002 | Moon et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | Williams et al. |
| 2002/0150909 A1 | 10/2002 | Stuelpnagel et al. |
| 2002/0168678 A1 | 11/2002 | Williams et al. |
| 2002/0172963 A1 | 11/2002 | Kelley et al. |
| 2002/0187515 A1 | 12/2002 | Chee et al. |
| 2003/0020334 A1 | 1/2003 | Nozu et al. |
| 2003/0032052 A1 | 2/2003 | Hadd et al. |
| 2003/0044799 A1 | 3/2003 | Matson |
| 2003/0044833 A1 | 3/2003 | Benchikh et al. |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0138809 A1 | 7/2003 | Williams et al. |
| 2003/0141929 A1 | 7/2003 | Casper et al. |
| 2003/0148301 A1 | 8/2003 | Aono et al. |
| 2003/0148344 A1 | 8/2003 | Rothberg et al. |
| 2003/0152929 A1 | 8/2003 | Howard |
| 2003/0152994 A1 | 8/2003 | Woudenberg et al. |
| 2003/0155942 A1 | 8/2003 | Thewes et al. |
| 2003/0157504 A1 | 8/2003 | Chee et al. |
| 2003/0175990 A1 | 9/2003 | Hayenga et al. |
| 2003/0186262 A1 | 10/2003 | Cailloux |
| 2003/0194740 A1 | 10/2003 | Williams |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0002470 A1 | 1/2004 | Keith et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2004/0207384 A1 | 10/2004 | Brederlow et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0093645 A1 | 5/2005 | Watanabe et al. |
| 2005/0095602 A1 | 5/2005 | West et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0142033 A1 | 6/2005 | Glezer et al. |
| 2005/0151181 A1 | 7/2005 | Beintner et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2005/0285155 A1 | 12/2005 | Johnson et al. |
| 2006/0000772 A1 | 1/2006 | Sano et al. |
| 2006/0016699 A1 | 1/2006 | Kamahori et al. |
| 2006/0024711 A1 | 2/2006 | Lapidus et al. |
| 2006/0035400 A1 | 2/2006 | Wu et al. |
| 2006/0040297 A1 | 2/2006 | Leamon et al. |
| 2006/0051807 A1 | 3/2006 | Fuller |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber |
| 2006/0289726 A1 | 12/2006 | Paulus et al. |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0099208 A1 | 5/2007 | Drmanac et al. |
| 2007/0099351 A1 | 5/2007 | Peters et al. |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138028 A1 | 6/2007 | Chodavarapu et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |

(56) References Cited

U.S. PATENT DOCUMENTS

| | | |
|---|---|---|
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0047836 A1 | 2/2008 | Strand et al. |
| 2008/0063566 A1 | 3/2008 | Matsumoto et al. |
| 2008/0077607 A1 | 3/2008 | Gatawood et al. |
| 2008/0085219 A1 | 4/2008 | Beebe et al. |
| 2008/0094074 A1 | 4/2008 | Kim et al. |
| 2008/0096216 A1 | 4/2008 | Quake |
| 2008/0111161 A1 | 5/2008 | Sorge et al. |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0136933 A1 | 6/2008 | Dosluoglu et al. |
| 2008/0145910 A1 | 6/2008 | Ward et al. |
| 2008/0164917 A1 | 7/2008 | Floyd et al. |
| 2008/0166727 A1 | 7/2008 | Esfandyarpour et al. |
| 2008/0176271 A1 | 7/2008 | Silver et al. |
| 2008/0178692 A1 | 7/2008 | Jung et al. |
| 2008/0185616 A1 | 8/2008 | Johnson et al. |
| 2008/0186093 A1 | 8/2008 | Forbes |
| 2008/0197022 A1 | 8/2008 | Suzuki et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286767 A1 | 11/2008 | Miyahara et al. |
| 2009/0026082 A1* | 1/2009 | Rothberg et al. ............ 204/556 |
| 2009/0030117 A1 | 1/2009 | Lanphere et al. |
| 2009/0032401 A1 | 2/2009 | Ronaghi et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0075838 A1 | 3/2009 | El Gamal et al. |
| 2009/0079414 A1 | 3/2009 | Levon et al. |
| 2009/0108831 A1 | 4/2009 | Levon et al. |
| 2009/0120905 A1 | 5/2009 | Kohl et al. |
| 2009/0121258 A1 | 5/2009 | Kumar |
| 2009/0127589 A1 | 5/2009 | Rothberg et al. |
| 2009/0127689 A1 | 5/2009 | Ye et al. |
| 2009/0140763 A1 | 6/2009 | Kim |
| 2009/0143244 A1 | 6/2009 | Bridgham et al. |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0201032 A1 | 8/2009 | Burdett et al. |
| 2009/0273386 A1 | 11/2009 | Korobeynikov et al. |
| 2009/0316477 A1 | 12/2009 | Horiuchi |
| 2010/0007326 A1 | 1/2010 | Nakazato |
| 2010/0026814 A1 | 2/2010 | Shimoda |
| 2010/0039146 A1 | 2/2010 | Park et al. |
| 2010/0052765 A1 | 3/2010 | Makino |
| 2010/0133547 A1 | 6/2010 | Kunze et al. |
| 2010/0137143 A1 | 6/2010 | Rothberg et al. |
| 2010/0156454 A1 | 6/2010 | Weir |
| 2010/0176463 A1 | 7/2010 | Koizumi et al. |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0255595 A1 | 10/2010 | Toumazou et al. |
| 2010/0273166 A1 | 10/2010 | Garcia |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0248320 A1 | 10/2011 | Rothberg et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001685 A1 | 1/2012 | Levine et al. |
| 2012/0001779 A1 | 1/2012 | Fife et al. |
| 2012/0012900 A1 | 1/2012 | Lee et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0168307 A1 | 7/2012 | Fife |
| 2012/0173159 A1 | 7/2012 | Davey et al. |
| 2012/0228136 A1 | 9/2012 | Levine |
| 2012/0247977 A1 | 10/2012 | Rothberg et al. |
| 2012/0249192 A1 | 10/2012 | Matsushita et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |
| 2013/0056353 A1 | 3/2013 | Nemirovsky et al. |
| 2013/0105868 A1 | 5/2013 | Kalnitsky et al. |
| 2013/0135018 A1 | 5/2013 | Kuo et al. |
| 2013/0210128 A1 | 8/2013 | Rothberg et al. |

(56) References Cited

U.S. PATENT DOCUMENTS

| | | |
|---|---|---|
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0281307 A1 | 10/2013 | Li et al. |
| 2013/0324421 A1 | 12/2013 | Rothberg et al. |
| 2013/0341734 A1 | 12/2013 | Merz |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235452 A1 | 8/2014 | Rothberg et al. |
| 2014/0235463 A1 | 8/2014 | Rothberg et al. |
| 2014/0308752 A1 | 10/2014 | Chang et al. |
| 2015/0097214 A1 | 4/2015 | Chen et al. |
| 2016/0178568 A1 | 6/2016 | Cheng et al. |

FOREIGN PATENT DOCUMENTS

| | | |
|---|---|---|
| CN | 1703623 | 11/2005 |
| CN | 1826525 | 8/2006 |
| CN | 101669026 | 3/2010 |
| CN | 101676714 | 3/2010 |
| CN | 102203282 | 9/2011 |
| CN | 102301228 | 12/2011 |
| CN | 102484267 | 5/2012 |
| DE | 4232532 | 4/1994 |
| DE | 4430811 | 9/1995 |
| DE | 19512117 | 10/1996 |
| DE | 102008012899 | 9/2009 |
| EP | 1975246 | 3/1984 |
| EP | 0223618 | 5/1987 |
| EP | 1243925 | 9/2002 |
| EP | 1243925 | 3/2003 |
| EP | 1371974 | 12/2003 |
| EP | 1432818 | 6/2004 |
| EP | 1542009 | 6/2005 |
| EP | 1557884 | 7/2005 |
| EP | 1669749 | 6/2006 |
| EP | 1870703 | 12/2007 |
| EP | 2307577 | 4/2011 |
| GB | 2457851 | 9/2009 |
| GB | 2461127 B | 7/2010 |
| JP | 58070155 | 4/1983 |
| JP | 62-237349 | 10/1987 |
| JP | 02-250331 | 10/1990 |
| JP | 02-310931 | 12/1990 |
| JP | H05-080115 | 4/1993 |
| JP | H10-078827 | 3/1998 |
| JP | 2000055874 | 2/2000 |
| JP | 2002-221510 | 8/2002 |
| JP | 2002272463 | 9/2002 |
| JP | 2003-279532 | 10/2003 |
| JP | 2003-322633 | 11/2003 |
| JP | 2004-510125 | 4/2004 |
| JP | 2005218310 | 8/2004 |
| JP | 2004-271384 | 9/2004 |
| JP | 2004-343441 | 12/2004 |
| JP | 05077210 | 3/2005 |
| JP | 2005-515475 | 5/2005 |
| JP | 2005-518541 | 6/2005 |
| JP | 2005-207797 | 8/2005 |
| JP | 06138846 | 6/2006 |
| JP | 2006-284225 | 10/2006 |
| JP | 2007/243003 | 9/2007 |
| JP | 2008-215974 | 9/2008 |
| JP | 2010513869 | 7/2010 |
| JP | 2011-525810 | 9/2011 |
| JP | 2012-506557 | 3/2012 |
| JP | 2015-506557 | 3/2012 |
| KR | 10-0442838 | 7/2004 |
| KR | 10-0455283 | 10/2004 |
| TW | 200510714 | 3/2005 |
| TW | 200946904 | 11/2009 |
| WO | WO-89/09283 | 10/1989 |
| WO | WO-98/13523 | 4/1998 |
| WO | WO-98/46797 | 10/1998 |
| WO | WO01/20039 | 3/2001 |
| WO | WO-01/42498 | 6/2001 |
| WO | 01/47804 | 7/2001 |
| WO | WO-01/81896 | 11/2001 |
| WO | WO-02/077287 | 10/2002 |
| WO | WO-02/086162 | 10/2002 |
| WO | PCT/JP2003/04697 | 4/2003 |
| WO | WO-03/073088 | 9/2003 |
| WO | 2004/017068 | 2/2004 |
| WO | WO-2004/040291 | 5/2004 |
| WO | WO2004040291 | 5/2004 |
| WO | WO2004048962 | 6/2004 |
| WO | 2004/081234 | 9/2004 |
| WO | WO2005015156 | 2/2005 |
| WO | 2005/022142 | 3/2005 |
| WO | WO-2005/047878 | 5/2005 |
| WO | WO2005043160 | 5/2005 |
| WO | WO-2005/054431 | 6/2005 |
| WO | WO2005602049 | 7/2005 |
| WO | 2005/073706 | 8/2005 |
| WO | WO-2005/084367 | 9/2005 |
| WO | WO2005090961 | 9/2005 |
| WO | WO-2006/005967 | 1/2006 |
| WO | WO-2006/022370 | 3/2006 |
| WO | 2006/056226 | 6/2006 |
| WO | WO2007002204 | 1/2007 |
| WO | WO-2007/086935 | 8/2007 |
| WO | WO-2008/007716 | 1/2008 |
| WO | WO-2008/058282 | 5/2008 |
| WO | 2008/076406 | 6/2008 |
| WO | 2008076406 | 6/2008 |
| WO | WO-2008/076406 | 6/2008 |
| WO | WO-2008/107014 | 9/2008 |
| WO | 2009/014155 | 1/2009 |
| WO | WO-2009/012112 | 1/2009 |
| WO | WO2009/014155 | 1/2009 |
| WO | WO2009041917 | 4/2009 |
| WO | WO2009074926 | 6/2009 |
| WO | WO2009081890 | 7/2009 |
| WO | WO-2009/158006 | 12/2009 |
| WO | WO-2010/008480 | 1/2010 |
| WO | WO-2010/047804 | 4/2010 |
| WO | WO-2010/047804 A8 | 4/2010 |
| WO | 2010/138186 | 12/2010 |
| WO | WO-2010/138182 | 12/2010 |
| WO | WO-2010/138188 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |
| WO | WO-2012/006222 | 1/2012 |
| WO | WO2012003359 | 1/2012 |
| WO | 2012/046137 | 4/2012 |
| WO | 2012/152308 | 11/2012 |

OTHER PUBLICATIONS

EP13174555.6 EP Extended Search Report Dec. 12, 2013.
EP13174555.6 EP Search Report Nov. 21, 2013.
EP13177039.8 EP Search Report Nov. 21, 2013.
EP13177590.0 EP Search Report Nov. 20, 2013.
Hammond, et al., "Performance and System-On-Chip Integration of an Unmodified CMOS ISFET", Science Direct, Sensors and Actuators vol. 111-112, 2005, pp. 254-258.
Ingebrandt, Sven et al., "Label-free Detection of DNA using Field-Effect Transistors", Phys. stat. sol. (a) 203, No. 14, 2006, pp. 3399-3411.
Wood, et al. "Base composition-independent hybridization in tetramethylammonium chloride: a method for oligonucleotide screening of highly complex gene libraries" Proc. Nat. Acad. Sci., 1985, pp. 1585-1588.
Chan, Wai P. et al., "An Integrated ISFETs Instrumentation System in Standard CMOS Technology", IEEE Journal of Solid-State Circuits, vol. 45, No. 9, 2010, pp. 1923-1934.
Chinese Patent Application 200780051353.2 Second Office Action Mailed Mar. 5, 2013.

(56) References Cited

OTHER PUBLICATIONS

Chung, W-Y. et al., "New ISFET Interface Circuit Design with Temperature Compensation", Microelectronics Journal, vol. 37(10), 2006, pp. 1105-1114.
Chung, W-Y. et al., "Temperature Compensation Electronics for ISFET Readout Applications", Biomedical Circuits and Systems, IEEE International Workshop Singapore, 2004, pp. 305-308.
Krause, M. et al., "Extended Gate Electrode Arrays for Extracellular Signal Recordings", Sensors and Actuators B, vol. 70, 2000, pp. 101-107.
Park, K-Y. et al., "ISFET Glucose Sensor System With Fast Recovery Characteristics by Employing Electrolysis", Sensors and Actuators B: Chemical, vol. 83 (1-3), 2002, pp. 90-97.
PCT/US2010/048835 International Preliminary Report on Patentability Mailed Mar. 19, 2013.
PCT/US2011/042668 International Preliminary Report on Patentability Mailed Mar. 26, 2013.
PCT/US2012/058996 International Search Report and Written Opinion Mailed Jan. 22, 2013.
PCT/US2012/071471 International Search Report and Written Opinion Mailed Apr. 24, 2013.
PCT/US2012/071482 International Search Report and Written Opinion Mailed May 23, 2013.
PCT/US2013/022140 International Search Report and Written Opinion Mailed May 2, 2013.
Pollack, J. et al. "Genome-Wide Analysis of DNA copy-number changes using cDNA Microarrays", Nature Genetics, vol. 23, 1999, pp. 41-46.
[No Author Listed], "ISFET Wikipedia article", Wikipedia, Last modified Nov. 7, 2006.
Ahmadian, A. et al., "Single-nucleotide polymorphism analysis by pyrosequencing", Anal. Biochem, vol. 280, 2000, pp. 103-110.
Akiyama, T et al., "Ion-Sensitive Field-Effect Transistors with Inorganic Gate Oxide for pH Sensing", IEE Transactions on Electron Devices, vol. ED-20(12), 1982, pp. 1936-1941.
AU2011226767 Search Information Statement Mailed Oct. 26, 2011, pp. 1-3.
Bandiera, L. et al., "A fully electronic sensor for the measurement of cDNA hybridization kinetics", Biosens Bioelectron, vol. 22, 2007, pp. 2108-2114.
Barbaro, M et al., "A CMOS, Fully Integrated Sensor for Electronic Detection of DNA Hybridization", IEEE Electron Device Letters, vol. 27(7), 2006, pp. 595-597.
Barbaro, M. et al., "A Charge-Modulated FET for Detection of Biomolecular Processes: Conception, Modeling, and Simulation", IEEE Transactions on Electron Devices, vol. 53(1), 2006, pp. 158-166.
Barbaro, M. et al., "Fully electronic DNA hybridization detection by a standard CMOS biochip", Sensors and Actuators B Chemical, vol. 118, 2006, pp. 41-46.
Bashford, G. et al., "Automated bead-trapping apparatus and control system for single-molecule DNA sequencing", Optics Express, vol. 16(5), Mar. 3, 2008, pp. 3445-3455.
Baumann, W. et al., "Microelectronic sensor system for microphysiological application on living cells", Sensors Actuators B, vol. 55, 1999, pp. 77-89.
Bausells, J. et al., "Ion-sensitive field-effect transistors fabricated in a commercial CMOS technology", Sensors and Actuators B Chemical, vol. 57, 1999, pp. 56-62.
Bergveld, P., "ISFET, Theory and Practice", IEEE Sensor Conference, Toronto, Oct. 2003, 2003, pp. 1-26.
Bergveld, P., "Thirty years of ISFETOLOGY What happened in the past 30 years and what may happen in the next 30 years", Sensors and Actuators B, vol. 88, 2003, pp. 1-20.
Besselink, G et al., "ISFET Affinity Sensor", Mehtods in Biotechnology, vol. 7: Affinity Biosensors: Techniques and Protocols, 1998, pp. 173-185.
Bobrov, P. et al., "Chemical sensitivity of an ISFET with Ta2O5 membrane in strong acid and alkaline solutions", Sensors and Actuators B, vol. 3, 1991, pp. 75-81.

Bousse, L. et al., "A process for the combined fabrication of ion sensors and CMOS circuits", IEEE Electron Device Letters, vol. 9(1), 1988, pp. 44-46.
Bousse, L. et al., "Zeta potential measurements of Ta2O5 and SiO2 thin films", J. Colloid Interface Sci., vol. 147(1), 1991, pp. 22-32.
Chen, Y. et al., "Nanoscale field effect transistor for biomolecular signal amplification", App Phys Letter, vol. 91, 2007, pp. 243511-1-243511-3.
Chen, Y. et al., "Silicon-based nanoelectronic field-effect pH sensor with local gate control", App Phys Letter, vol. 89, 2006, pp. 223512-1-223512-3.
Chou, J. et al., Letter to the Editor on "Simulation of Ta2O5 gate ISFET temperature characteristics", Sensors and Actuators B, vol. 80, 2001, pp. 290-291.
Chou, J. et al., "Simulation of Ta2O5 gate ISFET temperature charateristics", Sensor and Actuators B, vol. 71, Letter to the Editor, 2000, pp. 73-76.
Chung, W-Y et al., "ISFET interface circuit embedded with noise rejection capability", Electronics Letters, vol. 40(18), e-pub; 2 pages, 2004.
Chung, W-Y et al., "ISFET performance enhancement by using the improved circuit techniques", Sensors and Actuators B, vol. 113, 2006, pp. 555-562.
Eijkel, J. et al., "Measuring Donnan-related phenomena using a solid-state ion sensor and a concentration-step method", J. Membrane Sci., vol. 127, 1997, pp. 203-221.
Eijkel, J., "Potentiometric detection and characterization of adsorbed protein using stimulus-response measurement techniques", Thesis, Sep. 3, 1955, pp. 1-147; 160-192.
Eltoukhy, H et al., "A 0.18um CMOS 10-6 lux Bioluminescence Detection System-on-Chip", ISSCC 2004/Session12/Biomicrosystems/12.3, 2004, pp. 1-3.
Eltoukhy, H. et al., "A. 0.18-um CMOS Bioluminescence Detection Lab-on-Chip", IEEE J Solid-State Circuits, vol. 41(3), 2006, pp. 651-662.
EP7867780.4 Examination Report Mailed Jul. 3, 2012.
Eriksson, J. et al., "Pyrosequencing technology at elevated temperature", Electrophoresis, vol. 25, 2004, pp. 20-27.
Esfandyarpour, H. et al., "Gate-controlled microfluidic chamber with magnetic bead for DNA sequencing-by-synthesis technology", Proc 5th Intl Conf Nanochannels, Microchannels, Minnichannels, Puebla, Mexico (Jun. 18-20, 2007), Jun. 18, 2007, pp. 1-5.
Eversmann, B. et al., "A 128×128 CMOS Biosensor Array for Extracellular Recording of Neural Activity", IEEE J. Solid-State Circ., vol. 38(12), Dec. 12, 2003, pp. 2306-2317.
Faramarzpour, N. et al., "CMOS-Based Active Pixel for Low-Light Level Detection: Analysis and Measurements", IEEE Trans Electron Devices, vol. 54(12), Dec. 2007, pp. 3229-3237.
Finn, A et al., "Towards an Optimization of FET-Based Bio-Sensors", European Cells and Materials, vol. 4, Sup 2, 2002, pp. 21-23.
Fraden, J., "Handbook of Modern Sensors—Physics, Designs, and Applications . . . ", 17.3.2. CHEMFET Sensors, 1996, pp. 499-501.
Fritz, J. et al., "Electronic detection of DNA by its intrinsic molecular charge", PNAS, vol. 99(22), 2002, pp. 14142-14146.
GB0811656.8 Search and Examination Report Mailed Mar. 12, 2010.
GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracis, I. et al., "Test Structures for ISFET Chemical Sensors", Proc IEEE 1992 Intl Conf Microelec Test Struct, vol. 5, 1992, pp. 156-159.
Hammond, P. et al., "A System-on-Chip Digital pH Meter for Use in a Wireless Diagnostic Capsule", IEEE Transactons on Biomedical Engineering, vol. 52(4), 2005, pp. 687-694.
Hammond, P. et al., "Design of a Single-Chip pH Sensor Using a Conventional 0.6—μm CMOS Process", IEEE Sensors Journal, vol. 4(6), 2004, pp. 706-712.
Hammond, P. et al., "Encapsulation of a liquid-sensing microchip using SU-8 photoresist", MicoElectronic Engineering, vol. 73-74, 2004, pp. 893-897.

(56) References Cited

OTHER PUBLICATIONS

Hammond, S. et al., "Genomic sequencing and analysis of a Chinese Hamster ovary cell line using Illumine sequencing technology", *BMC Genomics*, vol. 12:67, 2011, pp. 1-8.
Han, Y., "Label-free detection of biomolecules by a field-effect transistor microarray biosensor with bio-functionalized gate surfaces", Masters Dissertation, 2006, pp. 1-63.
Hara, H. et al., "Dynamic response of a Ta2O5-gate pH-sensitive field-effect transistor", *Sensors Actuators B*, vol. 32, 1996, pp. 115-119.
Hermon, Z. et al., "Miniaturized bio-electronic hybrid for chemical sensing applications", *Tech Connect News*, Apr. 22, 2008, pp. 1.
Hideshima, S. et al., "Detection of tumor marker in blood serum using antibody-modified field effect transistor with optimized BSA blocking", *Sensors and Actuations B: Chemical*, vol. 161, 2012, pp. 146-150.
Hijikata, M. et al., "Identification of a Single Nucleotide Polymorphism in the MXA Gene Promoter (T/T at nt-88) Correlated with the Response of Hepatitis C Patients to Interferon", *Intervirology*, vol. 43, 2000, pp. 124-127.
Hizawa, T et al., "Fabrication of a two-dimensional pH image sensor using a charge transfer technique", *Sensors and Actuators B Chemical*, vol. 117, 2006, pp. 509-515.
Hizawa, T. et al., "32×32 pH Image Sensors for Real Time Observation of Biochemical Phenomena", *Transucers & Eurosensors '07*, 14th Intl. Conf. on Solid-Sate, Actuators and Microsystems, Lyon, Franc, Jun. 10-14, 2007, 2007, pp. 1311-1312.
Jakobson, C. et al., "Low frequency noise and drift in Ion Senstive Field Effect Transistors", *Sensors Actuators B*, vol. 68, 2000, pp. 134-139.
Ji, H. et al., "A CMOS contact imager for locating individual cells", *ISCAS*, 2006, pp. 3357-3360.
Ji, H. et al., "contact Imaging: Simulation and Experiment", *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), 2004, pp. 69-74.
Klein, M., "Time effects of ion-sensitive field-effect transistors", *Sens Act B*, vol. 17, 1989.
Koch, S et al., "Protein detection with a novel ISFET-based zeta potential analyzer", *Biosensors & Bioelectronics*, vol. 14, 1999, pp. 413-421.
Kruise, J. et al., "Detection of protein concentrations using a pH-step titration method", *Sensors Actuators B*, vol. 44, 1997, pp. 297-303.
Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.
Leamon, J. et al., "Cramming More Sequencing Reactions onto Microreactor Chips", *Chemical Reviews*, vol. 107, 2007, pp. 3367-3376.
Lee, C-S et al., "Ion-sensitive Field-Effect Transistor for Biological Sensing", *Sensors*, vol. 9, 2009, pp. 7111-7131.
Li, et al., "Sequence-Specific Label-Free DNA Sensors Based on Silico Nanowires", *Nano Letters,*, vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Proc. of the 1996 IEEE Intl. Conf. on Microelectronic Test Structures*, vol. 9, 1996, pp. 123-128.
Margulies, M. et al., "Genome sequencing in microfabricated high-density picolitre reactors", *Nature*, vol. 437(7057), 2005, pp. 376-380.
Marshall, A. et al., "DNA chips: an array of possibilities", *Nature Biotechnology*, vol. 16, 1998, pp. 27-31.
Martinoia, S. et al., "A behavioral macromodel of the ISFET in SPICE", *Sensors Actuators B*, vol. 62, 2000, pp. 182-189.

Martinoia, S. et al., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), 2006, pp. 1037-1044.
Milgrew, M. et al., "A 16×16 CMOS proton camera array for direct extracellular imaging of hydrogen-ion activity", *IEEE Intl Solid-State Circuits Conf*, Session 32:24, 2008, pp. 590-591; 638.
Milgrew, M. et al., "A large transistor based sensor array chip for direct extracellular imaging", *Sensors and Actuators B Chemical*, vol. 111-112, 2005, pp. 347-353.
Milgrew, M. et al., "Matching the transconductance characteristics of CMOS ESFET arrays by removing trapped charge", *IEEE Trans Electron Devices*, vol. 55(4), 2008, pp. 1074-1079.
Milgrew, M. et al., "Microsensor Array Technology for Direct Extracellular Imaging", Apr. 5, 2006, pp. 1-23.
Milgrew, M. et al., "The development of scalable sensor arrays using standard CMOS technology", *Sensors and Actuators B*, vol. 103, 2004, pp. 37-42.
Milgrew, M. et al., "The fabrication of scalable multi-sensor arrays using standard CMOS technology", *2003 IEEE Custom Integrated Circuits Conference*, 2003, pp. 513-516.
Miyahara, Y. et al., "Biochip Using Micromachining Technology", *J. Institute of Electrostatics*, Japan, vol. 27(6), 2003, pp. 268-272.
Miyahara, Y. et al., "Direct Transduction of Primer Extension into Electrical Signal Using Genetic Field Effect Transistor", *Micro Total Analysis Systems 2004*, vol. 1, 2004, pp. 303-305.
Miyahara, Y. et al., "Potentiometric Detection of DNA Molecules Using Field Effect Transistor", *The Japan Society of Applied Physics*, No. 3 (Translation included), 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, pp. 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Patolsky, F. et al., "Nanowire-Based Biosensors", *Analyt Chem 1*, vol. 78(13), 2006, pp. 4261-4269.
PCT/JP2005/001987 International Search Report Mailed Apr. 5, 2005.
PCT/JP2005/015522 International Preliminary Report on Patentability Mailed Mar. 19, 2007.
PCT/JP2005/015522 International Search Report Mailed Sep. 27, 2005.
PCT/US/2009/05745 International Preliminary Report on Patentability Issued Apr. 26, 2011.
PCT/US/2009/05745 International Search Report Mailed Dec. 11, 2009.
PCT/US/2009/05745 Written Opinion Mailed Dec. 11, 2009.
PCT/US2007/025721 International Preliminary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion Mailed Mar. 12, 2010.
PCT/US2010/001543 International Preliminary Report on Patentability Mailed Nov. 29, 2011, pp. 1-8.

(56) References Cited

OTHER PUBLICATIONS

PCT/US2010/001543 International Search Report and Written Opinion Mailed Oct. 13, 2010, pp. 1-12.
PCT/US2010/001553 International Preliminary Report on Patentability Mailed Dec. 8, 2011, pp. 1-10.
PCT/US2010/001553 International Search Report Mailed Jul. 28, 2010, pp. 1-2.
PCT/US2010/001553 Written Opinion Mailed Jul. 14, 2010, pp. 1-6.
PCT/US2010/48835 International Search Report and Written Opinion Mailed Dec. 16, 2010, pp. 1-12.
PCT/US2011/042655 International Search Report Mailed Oct. 21, 2011, pp. 1-2.
PCT/US2011/042660 International Search Report Mailed Nov. 2, 2011.
PCT/US2011/042665 International Search Report Mailed Nov. 2, 2011.
PCT/US2011/042668 International Search Report Mailed Oct. 28, 2011.
PCT/US2011/042683 International Search Report Mailed Feb. 16, 2012.
PCT/US2011/042683 Written Opinion Mailed Feb. 16, 2012.
Poghossian, A. et al., "Functional testing and characterization of ISFETs on wafer level by means of a micro-droplet cell", Sensor, vol. 6, 2006, pp. 397-404.
Pourmand, N et al., "Direct electrical detection of DNA synthesis", PNAS, vol. 103(17), 2006, pp. 6466-6470.
Pouthas, F. et al., "Spatially resolved electronic detection of biopolymers", Phys Rev, vol. 70, 2004, pp. 031906-1-031906-8.
Premanode, B. et al., "A composite ISFED readout circuit employing current feedback", Sensors Actuators B, vol. 127, 2007, pp. 486-490.
Premanode, B. et al., "A novel, low power biosensor for real time monitoring of creatine and urea in peritoneal dialysis", Sensors Actuators B, vol. 120, 2007, pp. 732-735.
Premanode, B. et al., "Ultra-low power precision ISFET readout using global current feedback", Electronic Lett, vol. 42(22), 2006, 2 pages.
Purushothaman, S. et al., "Protons and single nucleotide polymorphism detection: A simple use for the Ion Sensitive Field Effect Transistor", Sensors and Actuators B Chemical, vol. 114(2), 2006, pp. 964-968.
Purushothaman, S. et al., "Towards Fast Solid State DNA Sequencing", IEEE ISCAS 2002 Proceedings, Circuits and Systems, vol. 4, 2002, pp. IV-169-IV-172.
Rodriguez-Villegas, E., "Solution to trapped charge in FGMOS transistors", Electronics Letter, vol. 39(19), 2003.
Ronaghi, M. et al., "A Sequencing Method Based on Real-Time Pyrophosphate", Science, vol. 281, 1998, pp. 363-365.
Sakata, T. et al., "Cell-based field effect devices fo cell adhesion analysis", Intl. Conf. on Mecrotechnologies in Medicine and Biology, May 9-12, 2006, Okinawa, Japan, 2006, pp. 177-179.
Sakata, T. et al., "Detection of DNA recognition events using multi-well field effect transistor", Biosensors and Bioelectronics, vol. 21, 2005, pp. 827-832.
Sakata, T. et al., "Detection sensitivity of genetic field effect transistor combined with charged nanoparticle-DNA conjugate", Proc. of 2006 Intl. Conf. on Microtechnologies in Medicine and Biology, May 9-12, 2005, Okinawa, Japan, 2006, pp. 97-100.
Sakata, T. et al., "Direct detection of single nucleotide polymorphism using genetic field effect transistor", Digest of Papers Microprocesses and Nanotechnology 2004, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", Proc. of 3rd Ann. Intl. IEEE EMBS Special Topic Conf. on Microtechnologies in Medicine and Biology, Kahuku, Oahu, HI, May 12-15, 2005, 2005, pp. 219-222.
Sakata, T. et al., "Direct transduction of allele-specific primer extension into electrical signal using genetic field effect transistor", Biosensors and Bioelectronics, vol. 22, 2007, pp. 1311-1316.
Sakata, T. et al., "DNA Analysis Chip Based on Field-Effect Transistors", Japanese Journal of Applied Physics, vol. 44(4B), 2005, pp. 2854-2859.
Sakata, T. et al., "DNA Sequencing Based on Intrinsic Molecular Charges", Angewandte Chemie International Edition 2006, vol. 118, 2006, pp. 2283-2286.
Sakata, T. et al., "DNA Sequencing Based on Intrinsic Molecular Charges", Angewandte Chemie International Edition 2006, vol.45, 2006, pp. 2225-2228.
Sakata, T. et al., "DNA Sequencing Using Genetic field Effect Transistor", 13th Intl. Conf. on Solid-State Sensors, Actuators and Mircrosystems, Jun. 5-9, 2005, Seoul, Korea, 2005.
Sakata, T. et al., "Immobilization of oligonucleotide probes on Si3N4 surface and its application to genetic field effect transistor", Materials Science and Engineering: C, vol. 24, 2004, pp. 827-0832.
Sakata, T. et al., "Potential Behavior of Biochemically Modified Gold Electrode for Extended-Gate Feild-Effect Transistor", Japanese Journal of Applied Physics, vol. 44(4B), 2005, pp. 2860-2863.
Sakata, T. et al., "Potential Response of Genetic Field Effect Transistor to Charged Nanoparticle-DNA Conjugate", Digest of Papers Microprocesses and Nanotechnology 2005, Tokyo, Japan, 2005 Intl Microprocesses and Nanotech Conf., Hotel Bellclassic, 2005, pp. 42-43.
Sakata, T. et al., "Potentiometric Detection of Allele Specific Oligonucleotide Hybridization using Genetic Field Effect Transistor", Micro Total Analysis Systems 2004, 8th Intl. Conf. on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", Materials Research Society Symposium Proceedings, vol. 782, Micro- and Nanosystems, Dec. 1-3, 2003, Boston, Massachusetts, 2004, pp. 393-398.
Sakata, T. et al., "Potentiometric Detection of DNA Using Genetic Transistor", Denki Gakkai Kenkyukai Shiryo Chemical Sensor Kenkyukai, CHS-03-51-55, 2003, pp. 1-5.
Sakata, T. et al., "Potentiometric Detection of Single Nucleotide Polymorphism by Using a Genetic Field-effect transistor", ChemBioChem, vol. 6, 2005, pp. 703-710.
Sakurai, T. et al., "Real-Time Monitoring of DNA Polymerase Reactions by a Micro ISFET pH Sensor", Anal Chem, vol. 64(17), 1992, pp. 1996-1997.
Salama, K., "CMOS luminescence detection lab-on-chip: modeling, design, and characterization", Thesis, Presented at Stanford University, 2005, pp. ii-78.
Salama, K., "Modeling and simulation of luminescence detection platforms", Biosensors & Bioelectronics, 2004, pp. 1377-1386.
Sawada, K. et al., "A novel fused sensor for photo- and ion-sensing", Sensors Actuators B, vol. 106, 2005, pp. 614-618.
Sawada, K. et al., "Highly sensitive ion sensors using charge transfer technique", Sensors Actuators B, vol. 98, 2004, pp. 69-72.
Schasfoort, R. et al., "A new approach to immunoFET operation", Biosensors & Bioelectronics, vol. 5, 1990, pp. 103-124.
Schasfoort, R. et al., "Field-effect flow control for microfabricated fluidic networks", Science, vol. 286(5441), 1999, pp. 942-945.
Schoning, M. et al., "Bio FEDs (Field-Effect Devices): State-of-the-Art and New Directions", Electroanalysis, vol. 18(19-20), 2006, pp. 1893-1900.
SG200903992-6 Search and Examination Report Mailed Jan. 20, 2011.
Shah, N., "Microfabrication of a parellel-array DNA pyrosequencing chip", NNIN REU Research Accomplishments, 2005, pp. 130-131.
Shepherd, L. et al., "A biochemical translinear principle with weak inversion ISFETs", IEEE Trans Circuits Syst-I, vol. 52(12), Dec. 2005, pp. 2614-2619.
Shepherd, L. et al., "A novel voltage-clamped CMOS ISFET sensor interface", IEEE, 2007, pp. 3331-3334.

(56) References Cited

OTHER PUBLICATIONS

Shepherd, L. et al., "Towards direct biochemical analysis with weak inversion ISFETS", *Intl Workshop on Biomedical. . .* , 2004, S1.5-5-S1.5-8.

Shepherd, L. et al., "Weak inversion ISFETs for ultra-low power biochemical sensing and real-time analysis", *Sensors Actuators B*, vol. 107, 2005, pp. 468-473.

Shi, Y. et al., "Radical Capillary Array Electrophoresis Microplace and Scanner for High-Performance Nucleic Acid Analysis", *Anal. Chem.*, vol. 71(23), 1999, pp. 5354-5361.

Simonian, A. L. et al., "FET based biosensors for the direct detection of organophosphate neurotoxins", *Electroanalysis*, vol. 16(22), 2004, pp. 1896-1906.

Souteyrand, E. et al., "Direct detection of the hybridization of synthetic homo-oligomer DNA sequences by field effect", *J Phys Chem B*, vol. 101(15), 1997, pp. 2980-2985.

Starodub, N. et al., "Immunosensor for the determination of the herbicide simazine based on an ion-selective field-effect transistor", *Analytica Chimica Acta*, vol. 424, 2000, pp. 37-43.

Takenaka, S. et al., "DNA Sensing on a DNA Probe-Modified Electrode Using Ferrocenylnaphthalene Dimide as the Electrochmically Active Ligand", *Anal. Chem.*, vol. 72(6), 2000, pp. 1334-1341.

Tomaszewski, D. et al., "Electrical characterization of ISFETs", *J Telecomm Info Technol*, Mar. 2007, pp. 55-60.

Toumazou, C. et al., "Using transistors to linearase biochemistry", *Electronics Letters*, vol. 43(2), Jan. 18, 2007, 3 pages.

Truman, P., "Monitoring liquid transport and chemical composition in lab on . . . " *Lab on a Chip*, vol. 6, 2006, pp. 1220-1228.

Uslu, F. et al., "Labelfree fully electronic nucleic acid detection system based on a field-effect transistor device", *Biosens & Bioelectron*, vol. 19(12), 2004, pp. 1723-1731.

Van Der Wouden, E. et al., "Directional flow induced by synchronized longitudinal and zeta-potential controlling AC-electrical fields", *Lab Chip*, vol. 6(10), 2006, pp. 1300-1305.

Van Hal, R.E.G. et al., "A general model to describe the electrostatic potential at electrolyte oxide interfaces", *Advances in Colloid and Interface Science*, vol. 69, 1996, pp. 31-62.

Van Kerkhof, J. et al., "ISFET Responses on a stepwise change in electrolyte concentration at constant pH", *Sensors Actuators B: Chemical*, vol. 18-19, 1994, pp. 56-59.

Van Kerkhof, J. et al., "The ISFET based heparin sensor with a monolayer of protamine as affinity ligand", *Biosensors & Bioelectronics*, vol. 10(3), 1995, pp. 269-282.

Van Kerkhof, J., "The Development of an ISFET-based Heparin Sensor", *Thesis*, 1994.

Wagner, T et al., "'All-in-one' solid-state device based on a light-addressable potentiometric sensor platform", *Sensors and Actuators B*, vol. 117, 2006, pp. 472-479.

Wang, W. et al., "Label-free detection of small-molecule-protein interactions by using nanowire nanosensors", *Proc. of the Natl. Acad.of Sciences (PNAS)*, vol. 102(9), 2005, pp. 3208-3212.

Woias, P. et al., "Slow pH response effects of silicon nitride ISFET sensors", *Sensors and Actuators B*, vol. 48, 1998, pp. 501-504.

Woias, P., "Modelling the short time response of ISFET sensors", *Sensors and Actuators B*, vol. 24-25, 1995, pp. 211-217.

Wu, P. et al., "DNA and protein microarray printing on silicon nitride waveguide surfaces", *Biosensens Bioelectron*, vol. 21(7), 2006, pp. 1252-1263.

Xu, J-J et al., "Analytical Aspects of FET-Based Biosensors", *Frontiers in Bioscience*, vol. 10, 2005, pp. 420-430.

Yeow, T.C.W. et al., "A very large integrated pH-ISFET sensor array chip compatible with standard CMOS processes", *Sensor and Actuators B*, vol. 44, 1997, pp. 434-440.

Yuqing, M. et al., "Ion sensitive field effect trnasducer-based biosensors", *Biotechnology Advances*, vol. 21, 2003, pp. 527-534.

Zhang, X. et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, pp. v-viii.

Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.

Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.

EP09798251.6 Extended European Search Report dated Aug. 27, 2013.

EP11801437.2 Extended European Search Report dated Jul. 25, 2013.

EP11804218.3 Extended European Search Report dated Jul. 11, 2013.

EP11804218.3 First Office Action dated Jul. 29, 2013.

EP11827128.7 European Search Report dated Aug. 1, 2013.

EP13161312.7 Extended European Search Report dated Oct. 15, 2013.

EP13163995.7 Extended European Search Report dated Aug. 20, 2013.

EP13163995.7 First Office Action dated Aug. 30, 2013.

EP13164768.7 Extended European Search Report dated Aug. 20, 2013.

EP13164768.7 First Office Action dated Aug. 30, 2013.

Eriksson, J. et al. "Pyrosequencing Technology at Elevated Temperature" Electrophoresis, vol. 25, 2004, pp. 20-27.

Hanshaw, R. et al., "An indicator displacement system for fluorescent detection of phosphate oxyanions under physiological conditions" Science Direct, Tetrahedron Ltrs., vol. 45, 2004, pp. 8721-8724.

Hizawa, et al. "Sensing Characteristics of Charge Transfer Type pH Sensor by Accumulative Operation" IEEE Sensors, EXCO, Daegu, Korea, 2006, pp. 144-147.

JP20120246413 First Office Action dated Jun. 28, 2013.

Lee, S. et al. "An Enhanced Glucose Biosensor Using Charge Transfer Techniques" Biosensors and Bioelectronics, vol. 24, 2008, pp. 650-656.

Maki, W et al., "Nanowire-transistor based ultra-sensitive DNA methylation detection", Biosensors & Bioelectronics, vol. 23, 2008, pp. 780-787.

Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.

Milgrew, M. et al. "A Proton Camera Array Technology for Direct Extracellular Ion Imaging" IEEE International Symposium on Industrial Electronics, 2008, pp. 2051-255.

PCT/US2011/042683 International Preliminary Report on Patentability Mailed Jun. 4, 2013.

PCT/US2013/022129 International Search Report and Written Opinion dated Aug. 9, 2013.

Premanode, B. et al. "Drift Reduction in Ion-Sensitive FETs Using Correlated Double Sampling", Electronics Letters, IEEE Stevenage, GB, vol. 43 (16) Aug. 2, 2007.

Rothberg, J. et al., "An integrated semiconductor device enabling non-optical genome sequencing" Nature, vol. 475, No. 7356, 2011, pp. 348-352.

Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.

Voigt, H. et al. "Diamond-like carbon-gate pH-ISFET" Sensors and Actuators B., vol. 44, 1997, pp. 441-445.

Bockelmann, U. et al., "Detecting DNA by field effect transistor arrays", *Proceedings of the 2006 IFIP International Conference on Very Large Scale Integration*, 2006, 164-168.

EP11801439.8 EP Extended Search Report dated Mar. 7, 2014.

Tokuda, T. et al., "A CMOS image sensor with optical and potential dual imaging function for on-chip bioscientific applications", *Sensors and Actuators A*, vol. 125, No. 2, 2006, 273-280.

EP14152861.2 EP Search Report date Jul. 7, 2014.

Palan, B. et al., "New ISFET sensor interface circuit for biomedical applications", Sensors and Actuators B: Chemical: International

(56) References Cited

OTHER PUBLICATIONS

Journal Devoted to Research and Development of Physical and Chemical Transducers, Elsevier S.A. Ch., vol. 57, No. 1-3, 1999, pp. 63-68.
PCT/US2013/022129 International Preliminary Report on Patentability dated Jul. 22, 2014.
PCT/US2013/022140 International Preliminary Report on Patentability dated Jul. 22, 2014.
Zhao, B. et al., "Floating-Gate Ion Sensitive Field-Effect Transistor for Chemical and Biological Sensing", MRS Proceedings, vol. 828, 2004, pp. 349-354.
Dorf, Richard C. , "The electrical Engineering Handbook", *University of California, Davis, CRC Press, 2 edition, Chapter3—Linear Circuit Analysis*, Jun. 25, 2004, pp. 3-1 to 3-66.
EP09822323.3, "European Exteded Search Report", May 27, 2015, 8 pages.
Gardner, J.W. et al., "Enhancing electronic nose performance by sensor selection using a new integer-based genetic algorithm approach", *Science Direct, Sensors and Actuators B*, vol. 106, 2005, pp. 114-121.
Lin, B.J. et al., "Practicing the Novolac deep-UV portable conformable masking technique", *Journal of Vacuum Science and Technology*, Vo. 19, No. 4, 1981, 1313-1319.
Naidu, M. S. et al., "Introduction to Electrical Engineering", *Chapter 1—Fundamental Concepts of Electricity, McGraw Hill Education*(India) *Private Limited*, 1995, pp. 1-10.
Neaman, Donald A. , "Electronic Circuit Analysis and Disign", *McGraw Hill Higher Education, 2nd edition, Chapter 6—Basic FET Amplifiers*, (reference will be uploaded in 2 parts due to size) part 1 of 2, Dec. 1, 2000, pp. 313-345.
Neaman, Donald A. , "Electronic Circuit Analysis and Design", *McGraw Hill Higher Education, 2nd edition, Chapter 6—Basic FET Amplifiers*, (reference will be uploaded in 2 parts due to size) part 2 of 2, Dec. 1, 2000, pp. 346-381.
Nishiguchi, K. et al., "Si nanowire ion-sensitive field-effect transistors with a shared floating gate", *Applied Physics Letters* vol. 94, 2009, pp. 163106-1 to 163106-3.
PCT/US2007/025721, "Declaration of Non-Establishment of International Search Report", Jul. 15, 2008.
PCT/US2010/001553, "International Preliminary Report on Patentability", Dec. 8, 2011, 1-10.
PCT/US2010/001553, "International Search Report", Jul. 28, 2010, pp. 1-2.
PCT/US2010/001553, "Written Opinion", Jul. 14, 2010, pp. 1-6.
PCT/US2011/042669, "International Search Report", Jan. 09, 2012, pp. 1-5.
PCT/US2011/042669, "Written Opinion", Jan. 9, 2012, pp. 1-5.
PCT/US2014/020887, "International Search Report and Written Opinion", May 30, 2014, 12 pages.
PCT/US2014/020892, "International Search Report and Written Opinion mailed Jun. 3, 2014".
PCT/US2014/040923, "International Search Report and Written Opinion", Sep. 1, 2014, 14 pages.
Shi, Y. et al., "Radical Capillary Array Electrophoresis Microplace and Scanner for High-Performance Nucleic Acid Analysis", *Anal. Chem.*, vol. 71(23), 1999, 5354-5361.
Van Der Schoot, Bart et al., "The Use of a Multi-ISFET Sensor Fabricated in a Single Substrate", *Letter to the Editors, Sensors and Actuators*, vol. 12, 1987, pp. 463-468.
Van Kerkhof, "The Development of an ISFET based heparin sensor using the ion-step measuring method", *Biosensors and Bioelectronics*, vol. 9, Nos. 9-10, 1993, 463-472.
Vardalas, John , "Twists and Turns in the Development of the Transistor", *IEEE—USA Today's Engineer Online*, May 2003, 6 pages.
Wilhelm, D. et al., "pH Sensor Based on Differential Measurements on One pH-FET Chip", *Sensors and Actuators B*, vol. 4, 1991, pp. 145-149.
European Search Report for European Application No. EP15170247.9 mailed Nov. 10, 2015, 4 pages.
International Preliminary Report on Patentability for International Application No. PCT/US2014/040923 mailed Dec. 15, 2015, 8 pages.
Chin, Yuan-Lung et al., "Titanium Nitride Membrane Application to Extended Gate Field Effect Transistor pH Sensor Using VLSI Technology", *Jpn. J. Appl. Phys.* vol. 40, Part 1, No. 11, Nov. 2001, pp. 6311-6315.
International Preliminary Amendment on Patentability for International Application No. PCT/US2014/020887 mailed Sep. 15, 2015, 8 pages.
European Search Report for European Application No. EP10780935 mailed Jun. 9, 2015, 5 pages.
Supplementary European Search Report for European Application No. EP10780935 mailed Sep. 30, 2015, 6 pages.
Ligler, Frances S. et al., "Array biosensor for detection of toxins", *Anal. Bioanal Chem* vol. 377, 2003, pp. 469-477.
Matula, Richard A., "Electrical Resistivity of Copper, Gold, Palladium, and Silver", *Journal of Physical and Chemical Reference Data*, vol. 8.4, 1979, pp. 1147-1298.
Rowe, Chris A. et al., "An Array Immunosensor for Simultaneous Detection of Clinical Analytes", *Anal. Chem.* vol. 71, 1999, pp. 433-439.
European Search Report for European Application No. EP10780930 mailed Jun. 15, 2015, 3 pages.
European Search Report for European Application No. EP10857377 mailed Jun. 26, 2015, 3 pages.
Temes, G.C. et al., "A Tutorial Discussion of The Oversampling Method for A/D and D/A Conversion", *1990 IEEE International Symposium on Circuits and Systems*, vol. 2 of 4, 1990, 5 pages.
Thewes, R. et al., "CMOS-based Biosencor Arrays", *Proceedings of the Design, Automation and Test in Europe Conference and Exhibition*, 2005, 2 pages.
Yoshida, Shoji et al., "Development of a Wide Range pH Sensor based on Electrolyte-Insulator-Semiconductor Structure with Corrosion-Resistant Al2O3-Ta2O5 and Al2O3—ZrO2", *Journal of the Electrochemical Society* vol. 151(3), 2004, pp. H53-H58.
"0V5640 Datasheet Product Specification", ¼" color CMOS QSXGA (5 megapixel) image sensor with OmniBSI technology, May 1, 2011, p. 1, line 9 and pp. 2-7, paragraph 1.
Izuru, Shinmura, "Kojien", published by Owanami, Fourth Edition, 1991, 2683.
Liu, Yan et al., "An ISFET based sensing array with sensor offset compensation and pH sensitivity enhancement", Proc. of 2010 IEEE Int. Symp. on Circuits and Systems (ISCAS), ISBN: 978-1-4244-5308-5, Jun. 2, 2010, pp. 2283-2286.
Morgenshtein, Arkadiy et al., "Wheatstone-Bridge readout interface for ISFET/REFET applications", Sensors and Actuators B: Chemical, vol. 98, No. 1, Mar. 2004, pp. 18-27.
Moriizumi, Toyosaka, "Biosensors", *Oyo Buturi* (*monthly publication of the Japan Society of Applied Physics*), vol. 54, No. 2, Feb. 10, 1985, pp. 98-114.
Nakazato, Kazuo, "An Integrated ISFET Sensor Array", *Sensors*, vol. 9, No. 11, 2009, 8831-8851.
Nakazato, Kazuro et al., "28p-Y-7 ISFET sensor array integrated circuits based on standard CMOS process", *The 55th annual meeting of the Japan Society of Applied Physics*, ISBN: 978-4-903968-44-5, Mar. 27, 2008, p. 70.
Nakazato, Kazuro, "An Integrated ISFET Sensor Array", *Sensors*, Nov. 2009, vol. 9, No. 11, ISSN: 1424-8220, [online], Internet, URL, http://www.mdpi.com/1424-8220-9/11/8831/pdf, Nov. 2009, pp. 8831-8851.
PCT/US2015/066052, "International Search Report and Written Opinion of the International Searching Authority", Apr. 7, 2016, 19 pages.
Schroder, Dieter K., "6. Oxide and Interface Trapped Charges, Oxide Thickness", *Semiconductor Material and Device Characterization*, John Wiley & Sons, ISBN: 978-0-471-73906-7, Feb. 17, 2006, pp. 319-387.
Wen-Yaw, Chung A. et al., "New ISFET interface circuit design with tempreature Compensation", CiteSeerxe—URL: http://citeseerx.ist.psu.edu/viewdoc/download?doi=10.1.1.95.2321&rep=rep1&type=pdf, 2006, 1.

(56) References Cited

OTHER PUBLICATIONS

PCT/US2015/066052, International Preliminary Report on Patentability, dated Jun. 29, 2017, 1-16.
Eastman Kodak Company, "Image Sensor Solutions-Full-Frame CCD Image Sensor Performance Specification", www.physics.csbsju.edu/370/photometry/manuals/kaf-1001e.pdf, Feb. 19, 2001.
EP17167536.6, European Search Report dated Nov. 7, 2017, 1-13.
TW 106101966, Search Report dated Jan. 2, 2016, 1 pg.
JP2017-030653, Office Action, dated Feb. 15, 2018, 1-4.
TW103129092, Taiwan Search Report, dated Jan. 25, 2018, 1 pg.

\* cited by examiner

METHOD AND APPARATUS FOR IDENTIFYING DEFECTS IN A CHEMICAL SENSOR ARRAY

CROSS-REFERENCE TO RELATED APPLICATIONS

This application claims priority to U.S. Provisional Application No. 61/565,602 filed 1 Dec. 2012, the entire contents of which are incorporated by reference herein.

BACKGROUND

The present disclosure relates to sensors for chemical analysis, and more particularly to methods for testing a chemical sensor array for defects.

A variety of types of chemical sensors have been used in the detection of various chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance affects the threshold voltage of the chemFET, which can be measured to detect and/or determine characteristics of the chemical reaction. The threshold voltage may for example be measured by applying appropriate bias voltages to the source and drain, and measuring a resulting current flowing through the chemFET. As another example, the threshold voltage may be measured by driving a known current through the chemFET, and measuring a voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, usually due to the dissociation of oxide groups by the ions in the analyte solution. The change in surface potential at the sensitive area of the ISFET affects the threshold voltage of the device, which can be measured to indicate the presence and/or concentration of ions within the solution.

Arrays of ISFETs may be used for monitoring chemical reactions, such as DNA sequencing reactions, based on the detection of ions present, generated, or used during the reactions. See, for example, U.S. Pat. No. 7,948,015 to Rothberg et al., which is incorporated by reference herein. More generally, large arrays of chemFETs or other types of chemical sensors may be employed to detect and measure static and/or dynamic amounts or concentrations of a variety of analytes (e.g. hydrogen ions, other ions, compounds, etc.) in a variety of processes. The processes may for example be biological or chemical reactions, cell or tissue cultures or monitoring, neural activity, nucleic acid sequencing, etc.

The cost and effort associated with an experiment using a chemical sensor array can be significant. It is therefore desirable to provide techniques for accurately determining whether a chemical sensor array is functioning properly, prior to conducting an experiment.

SUMMARY

In one implementation, an apparatus is described that includes an array of sensors including a chemical sensor and a reference sensor. The chemical sensor is coupled to a reaction region for receiving at least one reactant, and the reference sensor includes a transistor having a control terminal coupled to a reference node. The apparatus further includes a controller to apply a bias voltage to the reference node to place the transistor in a known state. The controller further acquires an output signal from the reference sensor in response to the applied bias voltage. The controller further determines a defect associated with the array if the output signal does not correspond to the known state.

In another implementation, an apparatus is described that includes an array of sensors including a plurality of chemical sensors and a plurality of reference sensors. Each chemical sensor is coupled to a corresponding reaction region for receiving at least one reactant. Each reference sensor includes a field effect transistor having a gate coupled to a corresponding reference line. The apparatus further includes an access circuit for accessing the chemical sensors and the reference sensors. The apparatus further includes a controller to apply bias voltages to the reference lines to select corresponding reference sensors. The controller further acquires output signals from the selected reference sensors. The controller further identifies one or more defects in the access circuit based on differences between the acquired output signals and the expected output signals.

In yet another implementation, a method for operating an apparatus is described. The method includes applying a bias voltage to place a transistor of a reference sensor in a known state. The reference sensor is in an array of sensors that further includes a chemical sensor coupled to a reaction region for receiving at least one reactant. The method further includes acquiring an output signal from the reference sensor in response to the applied bias voltage. The method further includes determining a defect associated with the array if the output signal does not correspond to the known state.

Other implementations may include a non-transitory computer readable storage medium storing instructions executable by a processor to perform a method as described above. Yet another implementation may include a system including memory and one or more processors operable to execute instructions, stored in the memory, to perform a method as described above.

Particular aspects of one more implementations of the subject matter described in this specification are set forth in the drawings and the description below. Other features, aspects, and advantages of the subject matter will become apparent from the description, the drawings, and the claims.

DETAILED DESCRIPTION

Figure 1:
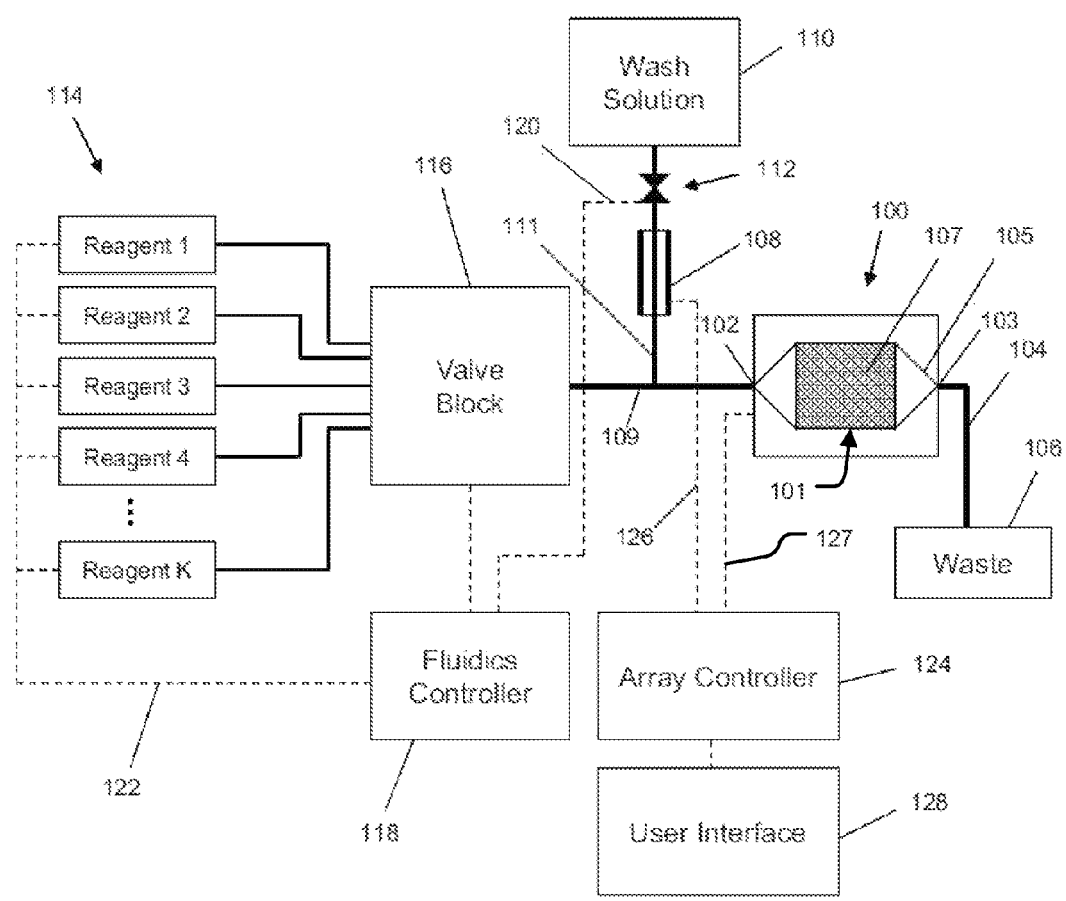
FIG. 1 illustrates a block diagram of components of a system for nucleic acid sequencing according to an exemplary embodiment.

Techniques are described herein for detecting and/or identifying defects associated with chemical sensor arrays, so that the experiments are not conducted using defective devices. These defects can include, among other things, defective column circuits and/or row circuits used to access the sensors in the array. If not detected, these defective circuits can result in incorrect data being collected when the array is used to conduct an experiment. By testing the array using the techniques described herein, the issues associated with the subsequent use of a defective sensor array can be reduced or eliminated.

Sensor arrays described herein include one or more reference sensors and one or more chemical sensors. A reference sensor includes a transistor which can be used to determine whether defects are associated with the array, prior to conducting an experiment. For example, in an experiment that includes flowing one or more solutions over the array, a reference sensor can allow the testing of the device containing the array, without exposing the array to solution. A reference sensor may for example have the same or similar structure as a chemical sensor, but lack the chemical sensitivity of the chemical sensor.

The chemical sensors may for example be chemically-sensitive field effect transistors (chemFETs), such as ion-sensitive field effect transistors (ISFETS). Examples of chemical sensors that may be used in embodiments are described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

Prior to using the array in an experiment, the output signals from one or more reference sensors can be collected and processed by a controller (e.g. a computer or other type of data processor) internal or external to the device containing the array. This processing includes determining whether defects are associated with the array as described herein.

In various exemplary embodiments, the methods, systems, and computer readable media described herein may advantageously ensure that properly functioning sensor arrays are used in subsequent experiments, such as electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a sensor can be determined.

FIG. 1 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 overlying a sensor array that includes chemical sensors and reference sensors arranged in rows and columns. The flow cell 101 includes an inlet 102, an outlet 103, and a flow chamber 105 defining a flow path of reagents over the microwell array 107.

The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, or other suitable methods, and may be discarded into the waste container 106 after exiting the outlet 103 of the flow cell 101. The fluidics controller 118 may control driving forces for the reagents 114 and the operation of valve 112 and valve block 116 with suitable software.

The microwell array 107 includes an array of reaction regions, also referred to herein as microwells, which are operationally associated with corresponding chemical sensors in the sensor array. For example, each microwell may be coupled to a chemical sensor suitable for detecting an analyte or reaction property of interest within that microwell. The microwell array 107 may be integrated in the integrated circuit device 100, so that the microwell array 107 and the sensor array are a single device or chip.

The flow cell 101 may have a variety of configurations for controlling the path and flow rate of reagents 114 over the microwell array 107. The array controller 124 provides bias voltages and timing and control signals to the integrated circuit device 100 for reading the reference sensors and chemical sensors of the sensor array. The array controller 124 also provides a reference bias voltage to the reference electrode 108 to bias the reagents 114 flowing over the microwell array 107.

Prior to beginning an experiment for nucleic acid sequencing, the array controller 124 collects and processes output signals from reference sensors of the sensor array through output ports on the integrated circuit device 100 via bus 127. As described in more detail below, this processing includes determining whether the integrated circuit device 100 is operating properly, or if it should be replaced with another device prior to beginning an experiment.

The user interface 128 may display information about the flow cell 101 and the output signals received from the integrated circuit device 100, including displaying messages notifying the user of any defects associated with the integrated circuit device 100. The user interface 128 may also display instrument settings and controls, and allow a user to enter or set instrument settings and controls.

During an experiment, the array controller 124 also collects and processes output signals from the chemical sensors of the sensor array. The array controller 124 may be a computer or other computing means. The array controller 124 may include memory for storage of data and software applications, a processor for accessing data and executing applications, and components that facilitate communication with the various components of the system in FIG. 1.

In an exemplary embodiment, during the experiment the fluidics controller 118 may control delivery of the individual reagents 114 to the flow cell 101 and integrated circuit device 100 in a predetermined sequence, for predetermined durations, at predetermined flow rates. The array controller 124 can then collect and analyze the output signals of the chemical sensors due to reactions occurring in response to the delivery of the reagents 114.

The values of the output signals of the chemical sensors indicate physical and/or chemical parameters of one or more reactions taking place in the corresponding microwells in the microwell array 107. For example, in an exemplary embodiment, the values of the output signals may be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No. 61/428,097, filed Dec. 29, 2010, which are all incorporated by reference herein in their entirety.

During the experiment, the system may also monitor and control the temperature of the integrated circuit device 100, so that reactions take place and measurements are made at a known predetermined temperature.

The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

Figure 2:
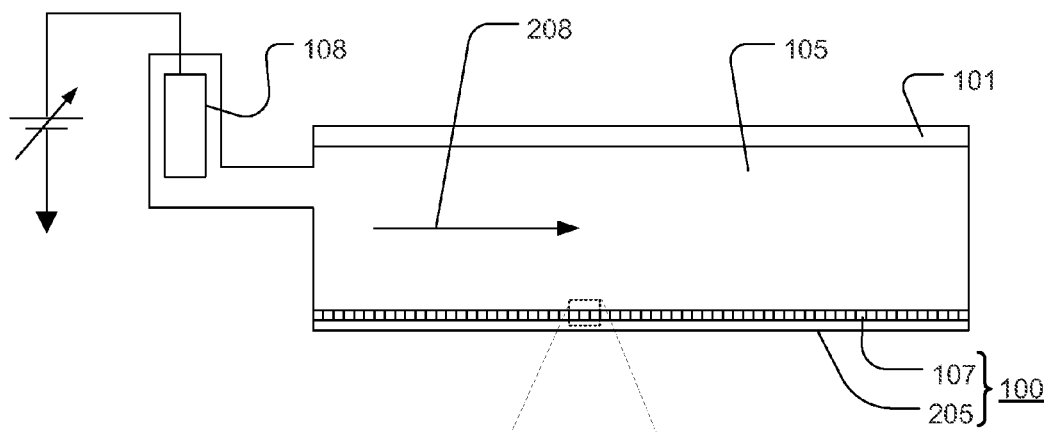
FIG. 2 illustrates cross-sectional and expanded views of a portion of the integrated circuit device and flow cell of FIG. 1.
Figure 2:
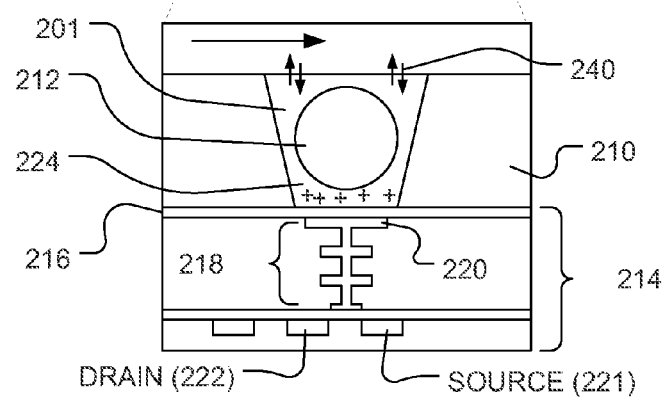

FIG. 2 illustrates cross-sectional and expanded views of a portion of the integrated circuit device 100 and flow cell 101. During operation, the flow chamber 105 of the flow cell 101 defines a reagent flow 208 of delivered reagents across open ends of the microwells in the microwell array 107. The volume, shape, aspect ratio (such as base width-to-well depth ratio), and other dimensional characteristics of the microwells may be selected based on the nature of the reaction taking place, as well as the reagents, byproducts, or labeling techniques (if any) that are employed.

The expanded view of FIG. 2 illustrates a representative microwell 201 in the microwell array 207, and a corresponding chemical sensor 214 in the sensor array 205. The sensor array 205 also includes one or more reference sensors (not shown).

The chemical sensor 214 can be a chemical field-effect transistor (chemFET), more specifically an ion-sensitive FET (ISFET), with a floating gate 218 having a sensor plate 220 separated from the microwell interior by an ion-sensitive layer 216. The sensor plate 220 may for example include multiple patterned layers of conductive material. The ion-sensitive layer 216 may for example be an oxide of an upper layer of conductive material of the sensor plate 220. Reactants, wash solutions, and other reagents may move in and out of the microwells by a diffusion mechanism 240.

The chemical sensor 214 can be responsive to (and generate an output signal related to) the amount of a charge 224 present on ion-sensitive layer 216 opposite the sensor plate 220. Changes in the charge 224 can cause changes in the threshold voltage of the chemFET, which can be measured by measuring the current between a source 221 and a drain 222 of the chemFET. In doing so, the chemFET can be used directly to provide a current-based output signal on an array line connected to the source 221 or drain 222, or indirectly with additional circuitry to provide a voltage-based output signal.

In an embodiment, reactions carried out in the microwell 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, multiple copies of the same analyte may be analyzed in the microwell 201 at the same time in order to increase the output signal generated. In an embodiment, multiple copies of an analyte may be attached to a solid phase support 212, either before or after deposition into the microwell 201. The solid phase support 212 may be microparticles, nanoparticles, beads, solid or porous comprising gels, or the like. For simplicity and ease of explanation, solid phase support 212 is also referred herein as a particle. For a nucleic acid analyte, multiple, connected copies may be made by rolling circle amplification (RCA), exponential RCA, or like techniques, to produce an amplicon without the need of a solid support.

Figure 3:
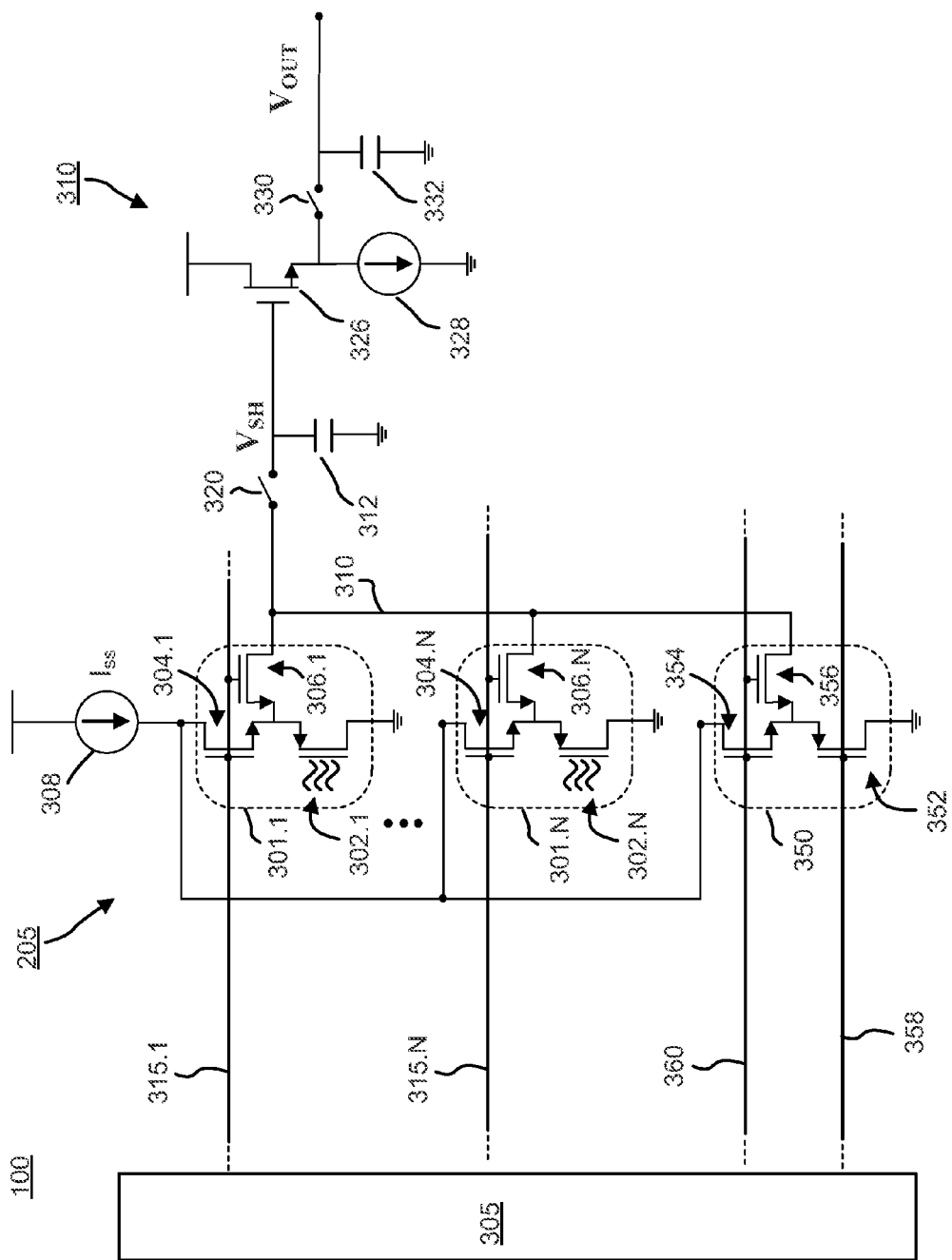
FIG. 3 illustrates a schematic diagram of a portion of a chemical sensor array according to an exemplary embodiment.

FIG. 3 illustrates a schematic diagram of a portion of the integrated circuit device 100 including the sensor array 205 with chemical sensors and reference sensors.

The integrated circuit device 100 includes an access circuit for accessing the chemical sensors and the reference sensors in the sensor array 205. In the illustrated example, the access circuit includes a row circuit 305 coupled to the sensor array 205 via row lines 315, 360 and a reference line 358. The access circuit also includes column circuits (e.g. column circuit 310) coupled to the sensor array 205 via column lines (e.g. column line 310).

The row circuit 305 and the column circuit 310 are responsive to timing and control signals provided by the array controller 124 in FIG. 1 to select various sensors and operate the sensor array 205 as described below. The array controller 124 also provides a reference bias voltage to the reference electrode (not shown) to bias the reagents flowing over the sensor array 205 during operation.

The sensors of the sensor array 205 are arranged in rows and columns. One column is shown in FIG. 3, and includes chemical sensors 301.1-301.N, representing a small section of the sensor array 205 that can include millions of sensors. N may be an integer number larger than one (e.g., 1024, . . . , 4096, etc.).

In the illustrated example in FIG. 3, a separate column circuit is coupled to each column of sensors in the array. Thus, as shown in FIG. 3, a column circuit 310 is used to provide the output signals of each sensor in the illustrated column. Alternatively, other arrangements of the sensors and column circuits may be used. For example, a single column circuit may be shared among sensors in multiple columns. As another example, a first column circuit may be coupled to a first set of sensors in a particular column, and a second column circuit may be coupled to a second set of sensors in the particular column.

In the illustrated embodiment, each chemical sensor (e.g., 301.1, ..., 301.N) includes a chemically-sensitive transistor (e.g., 302.1, ..., 302.N, respectively) and two row select switches (e.g., 304.1 and 306.1 for chemical sensor 301.1, or 304.N and 306.N for sensor 301.N, respectively). Each chemically-sensitive transistor 302.1 to 302.N has a gate terminal that may be coupled to a chemically-sensitive passivation layer arranged within a corresponding microwell. In some embodiments, the gate terminal includes a floating gate structure extending between a passivation layer and a gate oxide overlying the channel. During operation, the passivation layer may be exposed to an analyte solution to be analyzed. Overlying the gate terminal of each chemical sensor (e.g., on top of the passivation layer), there may be a respective microwell for holding the solution.

Each chemically-sensitive transistor 302.1 to 302.N has first terminals coupled to first sides of corresponding first row select switches 304.1 to 304.N, and second terminals coupled to ground in this example. Alternatively, the second terminals may be coupled to a bias voltage other than ground. In FIG. 3, the chemically-sensitive transistor 302.1 is a PMOS transistor with the first terminal (i.e. the source) connected to a first side of the first row select switch 304.1, and a second terminal (i.e., the drain) connected to ground. Each first row select switch (e.g., 304.1, ..., or 304.N) of each chemical detection pixel has a second side connected to a current source 108 used to provide a bias current during operation.

The first terminals of each chemically-sensitive transistor 302.1 to 302.N also serves as an output terminal of the respective chemical sensors 301.1 to 301.N and are coupled to a column line 310 via corresponding second row select switches 306 (e.g., 306.1 to 306.N). As shown in FIG. 3, each pair of row select switches 304 and 306 (e.g., 304.1 and 306.1) is coupled to the row select circuit 305 via respective row lines 315 (e.g. 315.1 to 315.N).

In a read operation of a selected chemical sensor 301.1, the row select circuit 305 facilitates providing a bias voltage to the row line 315.1 sufficient to turn on the row select switches 304.1 and 306.1. Turning on the row select switch 304.1 couples the selected chemical sensor 301.1 to a current source 108 which provides a bias current through the chemically-sensitive transistor 302.1. This in turn establishes a voltage at the output terminal of the chemically-sensitive transistor 302.1 based its threshold voltage, and thus based on characteristics or properties of an analyte of interest. Turning on the row select switch 306.1 couples the output terminal of the selected chemically-sensitive transistor 302.1 to the column line 310.

The column circuit 310 is coupled to the column line 310 for outputting an output signal $V_{OUT}$ based on the voltage at the output terminal of the chemically-sensitive transistor 302.1. In the illustrated embodiment, the column output circuit 310 includes a sample and hold switch 320, a sample and hold capacitor 312, an output transistor 326, an output current source 328 used to bias the output transistor 326, a column select switch 330, and a column capacitor 332. Alternatively, other configurations for the column circuit may be used.

The sample and hold switch 320 is responsive to a sample and hold signal to selectively couple the sample and hold capacitor 312 to the column line 310. Doing so stores a voltage $V_{SH}$ on the capacitor 312 based on the voltage at the output terminal of the chemically-sensitive transistor 302.1 of the selected chemical sensor 301.1. When the sample and hold switch 320 is open, it provides isolation from the selected chemical sensor 301.1 during readout of the voltage $V_{SH}$ on the capacitor 312.

The column select switch 330 is responsive to a column select signal to couple the output transistor 326 to the column capacitor 332 to readout the voltage $V_{SH}$. When the column select switch 330 is closed, the output transistor 326 produces an output signal $V_{OUT}$ of the selected chemical sensor 301.1 on the column capacitor 332 based on the voltage $V_{SH}$. The column capacitor 312 may be a discrete capacitor, and/or represent inherent capacitance of the column bus.

As mentioned above, the sensor array 205 also includes reference sensors to facilitate detection and/or identification of defects as described herein. The detection of the defects may be performed during an evaluation process, prior to use of the chemical sensors of the sensor array 205 in an experiment. In the illustrated example, the sensor array 205 includes reference sensor 350 within the same column as the chemical sensors chemical sensors 301.1~301.N.

The reference sensor 350 in this example includes a reference transistor 352 and a pair of reference select switches 354 and 356. The control terminal of the reference transistor 352 is coupled to the row circuit 305 via a reference line 358. In the illustrated example, the reference transistor is a field effect transistor with a gate terminal coupled to the reference line 358. The gates of the reference select switches 354 and 356 are coupled to the row circuit via a row line 360.

During the evaluation process, the row select circuit 305 facilitates providing a voltage to the row line 360 sufficient to turn on the reference select switches 354 and 356. The row select circuit 305 further facilitates providing a voltage to the reference line 358 sufficient to place the reference transistor 352 in a known state. This known state may for example be an off state (i.e. non-conducting) or an on state (i.e. conducting) of the reference transistor 352.

Turning on the reference select switch 354 couples the reference sensor 350 to the current source 308 to induce a bias current through the reference transistor 352. This in turn establishes a voltage at the output terminal (i.e. the source terminal in this example) of the reference transistor 352 based on the known state of the reference transistor 352. For example, if the voltage applied to the reference line 358 is sufficient to turn on the reference transistor 352, the voltage at the output terminal of the reference transistor 352 will be pulled low. Otherwise, the voltage at the voltage at the output terminal will be high.

Turning on the reference select switch 356 couples the output terminal of the reference transistor 352 to the column line 310. Similar to the discussion above, the column output circuit 310 can then generate an output signal $V_{OUT}$ based on the voltage at the output terminal of the reference transistor 352.

A defect associated with the integrated circuit device 100 can then be determined by comparing the value of the output signal $V_{OUT}$ to an expected range of values corresponding to the known state of the reference transistor 352. If the voltage of the output signal $V_{OUT}$ does not correspond to the known state, this indicates one or more defects may be present in the row circuit 30, the column circuit 310, and/or in the reference sensor 350 itself. These defects can prevent the integrated circuit device 100 from operating properly during a subsequent experiment. These defects may due to problems with the fabrication and/or assembly of the integrated circuit device 100.

Figure 4:
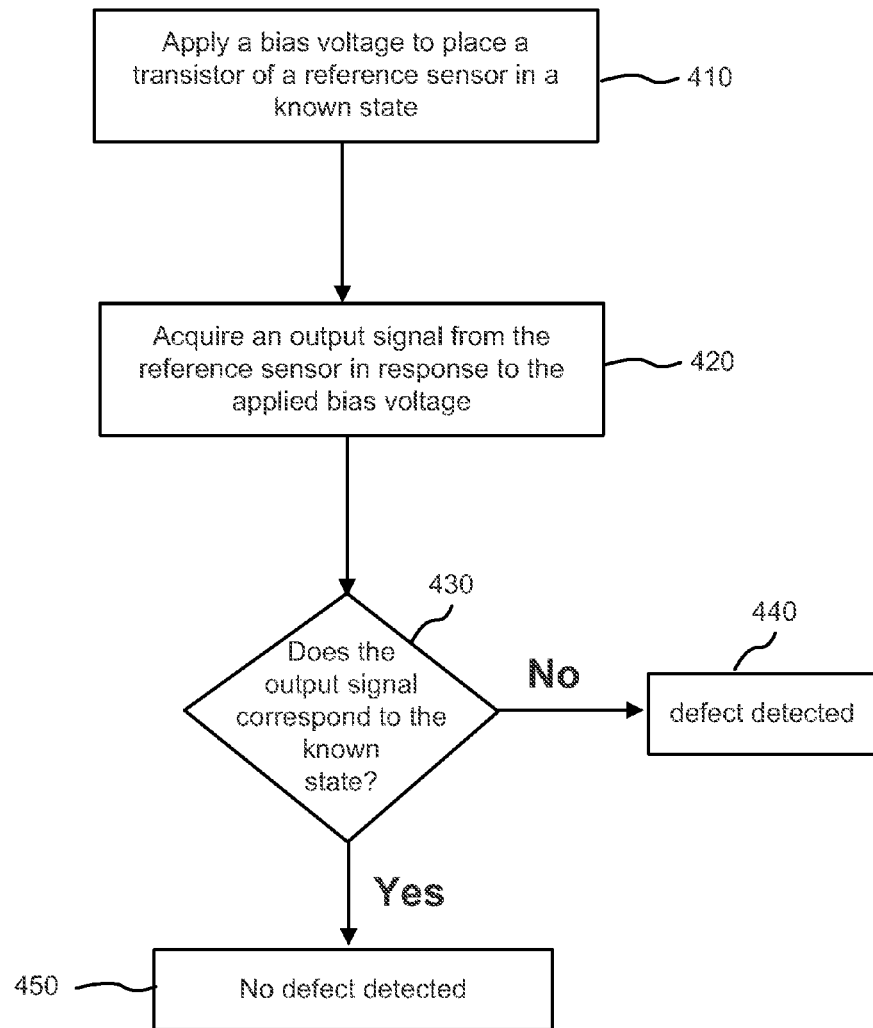
FIG. 4 is a flow chart of an example process for detecting a defect associated with a sensor array according to an exemplary embodiment.

FIG. 4 is a flow chart of an example process for detecting a defect associated with a sensor array according to an exemplary embodiment. Other embodiments may perform the steps in different orders and/or perform different or additional steps than the ones illustrated in FIG. 4. For convenience, FIG. 4 will be described with reference to a system that performs the process. The system can be for example, the system of FIG. 1.

At step 410, a bias voltage is applied to place a transistor of a reference sensor of an integrated circuit device in a known state. The reference sensor is part of a sensor array which includes a chemical sensor, such as those described above. The known state may for example be an off state or an on state of the transistor.

At step 420, an output signal from the reference sensor is acquired in response to the applied bias voltage.

At step 430, the system determines whether the output signal corresponds to the known state. This determination can be made by comparing the value of the acquired output signal to an expected range of values. The expected range of values can vary from embodiment to embodiment, and may for example be determined empirically.

If the output signal does not correspond to the known state, this indicates that a defect exists and the process continues step 440. In one embodiment, if a defect is detected, a message is displayed notifying the user of the defect. In yet another embodiment, the message displayed to the user is to not use the integrated circuit device in a subsequent experiment.

If the output signal does correspond to the known state, no defect has been detected and the process continues to step 450. After step 450, the integrated circuit device may then be used for a subsequent experiment. This experiment can include using the sensor array of the integrated circuit device for nucleic acid sequencing as described above.

In embodiments in which the integrated circuit device includes multiple reference sensors, each reference sensor may be operated using the process of FIG. 4. In such a case, the total number of detected defects may be counted. This total number of defects can then be compared to a predetermined number to determine whether the device should be used in a subsequent experiment. For example, if the total number of defects exceeds the predetermined number, a message may be displayed advising the user to scrap the integrated circuit device.

Figure 5:
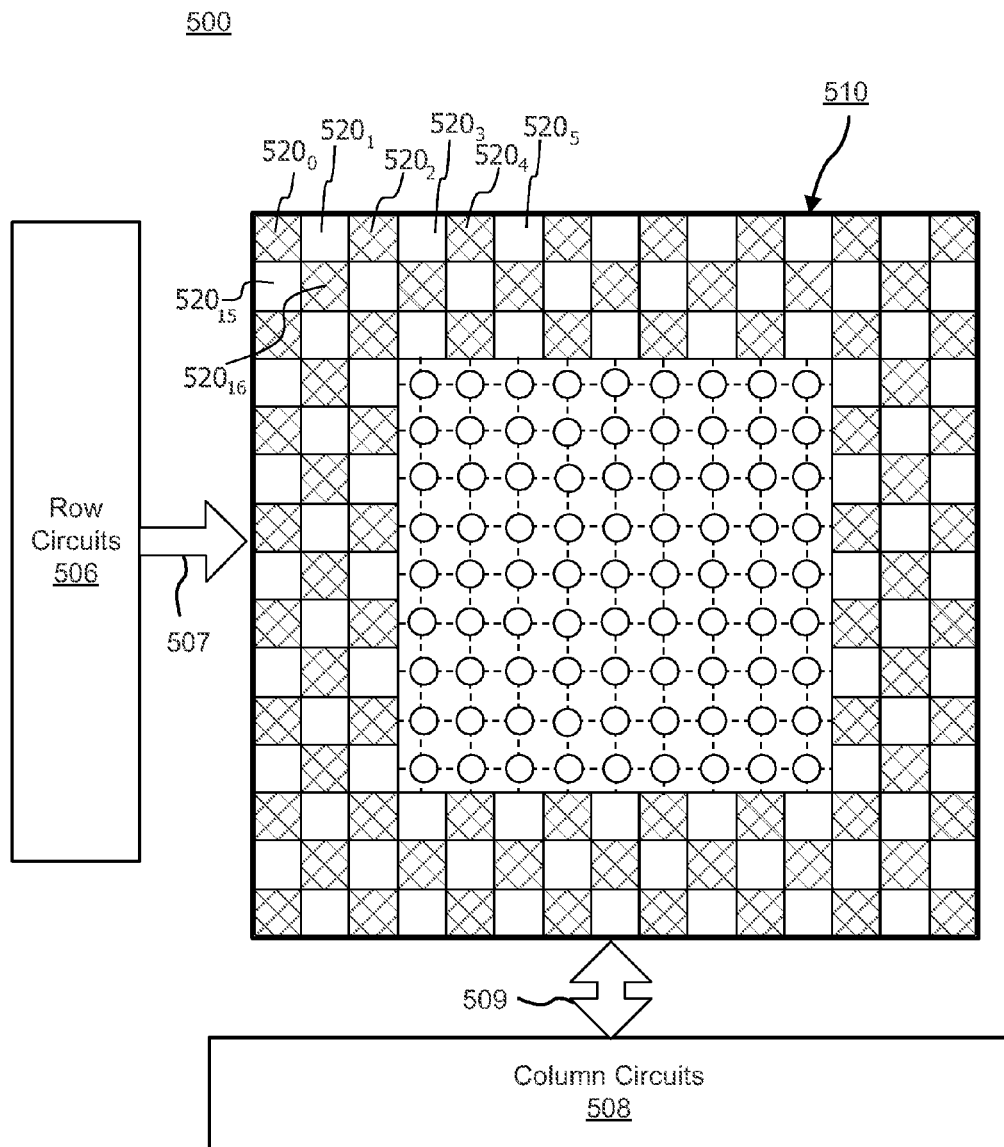
FIG. 5 illustrates a schematic diagram of a sensor array with first and second sets of reference sensors arranged along the periphery of the array.

FIG. 5 illustrates a simplified block diagram of an integrated circuit device 500 including a sensor array 510 with first and second sets of reference sensors 520 arranged along the periphery of the array.

The integrated circuit device 500 includes a row circuits 506 and column circuits 508 for reading the output signals from the sensors in the sensor array 510 via array lines 507 and 509 (e.g. row line, reference lines, and column lines). The row circuits 506 and column circuits 508 read the sensors in response to timing and control signals provided by an array controller (not shown in FIG. 5).

In the illustrated example, the reference sensors 520 are located at the periphery of the sensor array 510. The reference sensors 520 (depicted in FIG. 5 as squares) and the chemical sensors (depicted in FIG. 5 as circles) are arranged in rows and columns. In this example, the sensor array 510 includes 81 chemical sensors arranged into 9 rows and 9 columns. As also shown in FIG. 5, the reference sensors 520 are arranged in the top three rows, bottom three rows, left-most three columns, and right-most three columns of the sensor array 510. Alternatively, the arrangement and the number of the reference sensors 520 and the chemical sensors may be different.

In the illustrated example, the reference sensors 520 have the same structure as the chemical sensors. That is, each reference sensor 520 includes a transistor coupled to a microwell. However, the reference sensors 520 are not used to detect analytes in solution during the normal operation of the integrated circuit device 500. Rather, the gate terminals of the transistors of the reference sensors 520 are coupled to the row circuits 506 via array lines 507 (e.g. reference lines) to facilitate preliminary test/evaluation data, offset determination, and/or array calibration of the sensor array 510 as described herein.

In FIG. 5, chemical sensors and reference sensors 520 in each column of sensor array 510 are electronically coupled to one another via a common column line and share a dedicated column circuit within block 508. In this example, the drain terminal of each of the chemical sensors and reference sensors 520 along a given column are electrically coupled to one another, similar to the arrangement shown in FIG. 3.

Similarly, chemical sensors and reference sensors along a given row of the array 510 are coupled to a common row line and common row circuit in block 506 used to activate row select switches for each sensor along the given row. Therefore, with a unique row-column addressing signal input into column circuits 508 and row circuits 506, each of the chemical sensors and reference sensors 520 in the sensor array 510 can be individually accessed and read. For instance, reference sensors $520_0$, $520_1$, $520_{15}$, and $520_{16}$ can be individually accessed via a column circuit in block 508 and a row circuit in block 506 with unique row-column addressing signals.

In FIG. 5, transistors of alternating reference sensors 520 along a given row have their gate terminals tied to a first reference line and the remaining reference pixels along the same common row have their gate terminals tied to a second reference line. The first and second reference lines can be supplied with separate bias voltages generated by on-chip circuitry, or by an external power supply to the integrated circuit device.

In summary, gate terminals of reference sensors $520_0$, $520_2$, $520_4$, and so forth (e.g., alternating reference sensors depicted as white squares along the top row) are tied to the first reference line and gate terminals of reference sensors $520_1$, $520_3$, $520_5$, and so forth (e.g., alternating reference sensors depicted as hashed squares along the top row) are tied to the second reference line. This arrangement is replicated for each row of reference sensors 520 in sensor array 510, in which the gate terminals of half of the reference sensors 520 are tied to the first reference line and the gate terminals of the other half of the reference sensors 520 are tied to the second reference line.

As described in more detail below with reference to FIG. 6, with this alternating arrangement of reference sensors 520, the sensor array 510 can be tested to simultaneously identify defective column circuits, defective row circuits, and/or defective reference sensors. That is, the type of defect can be determined.

Figure 6:
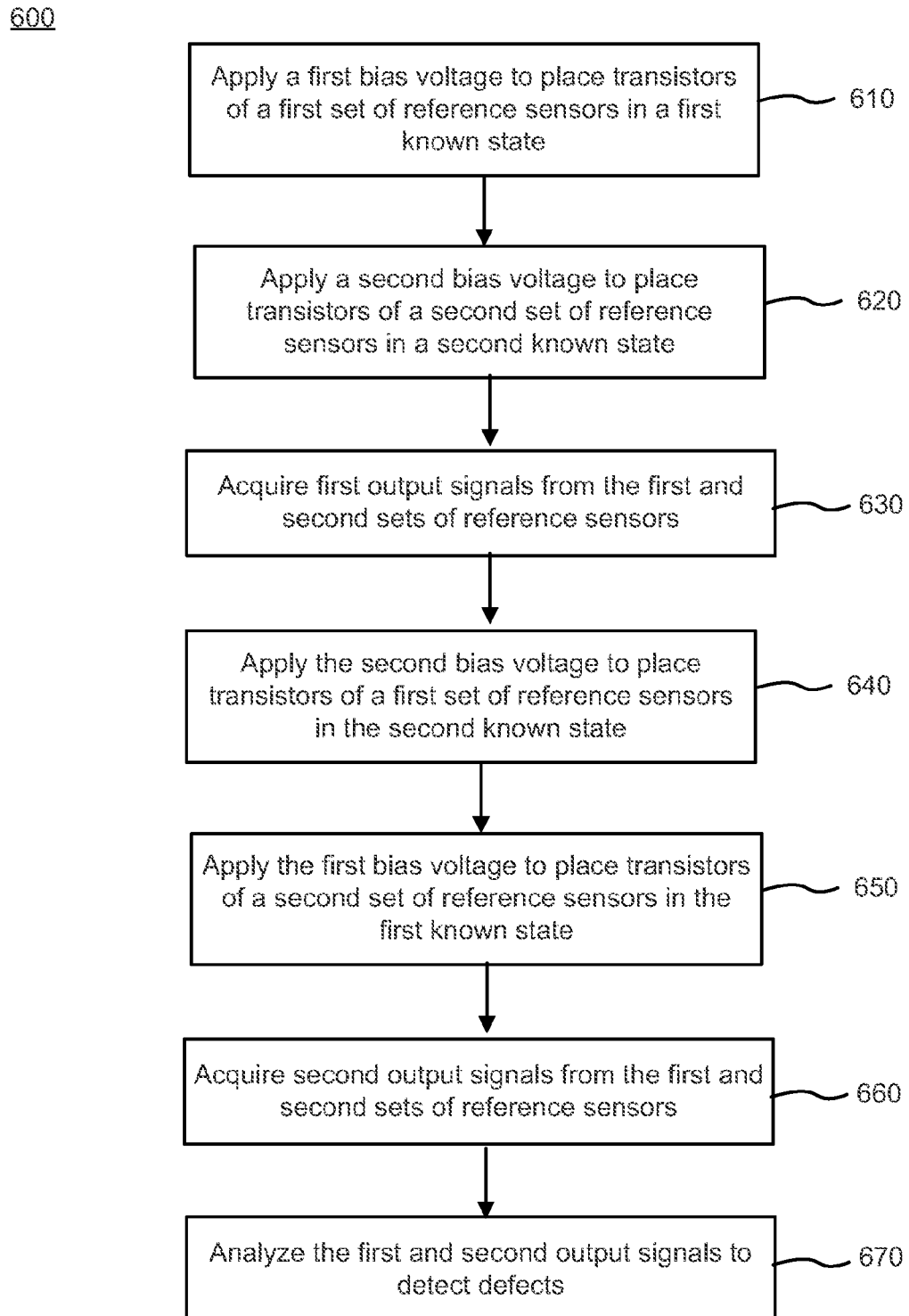
FIG. 6 is a flow chart of an example process for determining whether defects are associated with the sensor array of FIG. 5 according to an exemplary embodiment.

FIG. 6 is a flow chart of an example process for determining whether defects are associated with the sensor array of FIG. 5 according to an exemplary embodiment. Other embodiments may perform the steps in different orders and/or perform different or additional steps than the ones illustrated in FIG. 6.

In step 610, a first bias voltage is applied to the gate terminals of transistors of a first set of reference sensors to place these transistors in a first known state. In this example, the first bias voltage is a voltage level sufficient to turn "ON" the transistors of the first set of reference sensors. For example, if a reference sensor in the first set includes an n-channel transistor with its source terminal coupled to ground, the first bias voltage is above the threshold voltage of the n-channel transistor.

In step 620, a second bias voltage is applied to gate terminals of a second set of reference sensors to place these transistors in a second known state. In this example, the second bias voltage is a voltage level sufficient to turn "OFF" the transistors of the second set of reference sensors. For example, if a reference sensor in the first set includes an n-channel transistor with its source terminal coupled to ground, the second bias voltage is less than the threshold voltage of the n-channel transistor (e.g. zero volts or a negative voltage).

Based on the physical dimensions, electrical characteristics, and voltage applied to the gate terminals of the transistors in the reference sensors, an expected voltage value or voltage range can be calculated and/or measured for both ON and OFF states.

In step 630, first output signals of the first and second sets of reference sensors are read out using access circuits. For instance, with reference to FIG. 5, the reference sensors 520 are read out using the column circuits 508 and row circuits 506.

In a properly functioning array, the first output signals from the first set of reference sensors correspond to the first known state. Similarly, the first output signals from the second set of reference sensors correspond to the second known state if the array is functioning properly. In an embodiment, the first output signals from the first and second sets of reference sensors can be stored in a memory device, either on-chip or off-chip, for later processing and/or analysis to detect defects.

Next, in step 640, the second bias voltage is applied to gate terminals of the first set of reference sensors to place these transistors in the second known state. As described above, in this example, the second bias voltage is a voltage level sufficient to turn "OFF" the transistors of the first set of reference sensors.

In step 650, the first bias voltage is applied to gate terminals of the second set of reference sensors to place these transistors in the first known state. As described above, in this example, the first bias voltage is a voltage level sufficient to turn "ON" the transistors of the second set of reference sensors.

In step 660, second output signals of the first and second sets of reference sensors are read out. In a properly functioning array, the second output signals from the first set of reference sensors corresponding to the second known state. Similarly, the second output signals from the second set of reference sensors correspond to the first known state if the array is functioning properly.

In step 670, the first and second output signals are analyzed to detect defects. Defects in the array can include, for example but not limited to, a defective row circuit, a defective column circuit, and/or a defective reference sensor.

The identification of a defective row circuit can be made if all of the reference sensors in a corresponding particular row produce first and/or second output signals with unexpected or errant values. For instance, the first set of reference sensors in step 610 and the second set of reference pixels in step 650 are applied a voltage sufficient to turn ON the transistors in these reference sensors. If during these steps, none of the reference sensors in the particular row produce output signals which correspond to the ON state, this is an indication that the row circuit for that particular row is defective.

The identification of a defective column circuit can be made in a similar manner. That is, a defective column circuit can be identified if all of the reference sensors from a corresponding particular column produce first and/or second output signals having unexpected or errant values.

The first and second output signals may also be analyzed to determine whether individual reference sensors are defective. For example, a given reference sensor can be identified as defective by comparing its first output signal to its second output signal. For instance, if the output signal of the given reference sensor does not change in value between the application of the first bias voltage and the application of the second output signal, this is an indication that the given reference sensor is defective.

A defective reference sensor may also be identified if adjacent reference sensors provide output signals indicating that the access circuits for that reference sensor are functioning properly. For instance, with reference to FIG. 5, if reference sensor $520_1$ and $520_{15}$ provide output signals within the expected ranges, and reference sensor $520_{16}$ provides one or more output signals outside the expected ranges, this is an indication that the reference sensor $520_{16}$ is defective. That is because, since reference sensor $520_1$ provides a proper output signal, this in an indication that the column circuit shared by the column of sensors (including reference sensor $520_1$ and reference sensor $520_{16}$) is functioning properly. Also, since reference sensor $520_{15}$ provides a proper output signal, this is an indication that the row circuit for that row is functioning properly—reference sensor $520_{15}$ and $520_{16}$ share a common row circuit. Therefore, since the row and column circuits associated with the row and column containing the reference sensor $520_{16}$ produce proper output signals for at least some of the reference sensors in that row and that column, this is an indication that the reference sensor $520_{16}$ itself is defective.

Similar to the discussion above with respect to FIG. 4, in some embodiments the total number of detected defects may be counted. The total number of defects can then be compared to a predetermined number to determine whether the device can be used in a subsequent experiment. If the total number of defects exceeds the predetermined number, a message may be displayed to the user is to scrap the integrated circuit device. Alternatively, other techniques may be used to prevent the use of the defective integrated circuit device.

In some embodiments, the types of defects are each counted individually and compared to corresponding predetermined numbers to determine whether the device should used in a subsequent experiment. For instance, the total number of defective column circuits, the total number of defective row circuits, and the total number of defective reference sensors may be counted individually. In some embodiments, if the total number of defects for any defect type exceeds its respective predetermined number, a message may be displayed to the user is that integrated circuit device is defective and should not be used in the subsequent experiment.

The techniques described herein may be used with various nucleic acid sequencing techniques and apparatuses, including those described in U.S. Patent Application Publication No. 2010/0300559, No. 2010/0197507, No. 2010/0301398, No. 2010/0300895, No. 2010/0137143, and No. 2009/

0026082, and U.S. Pat. No. 7,575,865. Such sequencing platforms may involve sequencing-by-synthesis techniques that operate by the detection of inorganic pyrophosphate or hydrogen ions produced by nucleotide incorporation reactions. In some cases, the sensor array is a chemFET sensor array. In some cases, the chemFET sensors of the sensor array detect hydrogen ions. In some cases, flowing of the reagent(s) onto the sensor array causes chemical reactions that release hydrogen ions. In some cases, the amplitude of the signals from the chemFET sensors is related to the amount of hydrogen ions detected.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. An apparatus, comprising:
    an array of sensors including
        a chemical sensor coupled to a reaction region for receiving at least one reactant, the chemical sensor including a chemically-sensitive transistor, a first terminal of the chemically-sensitive transistor directly coupled to a first row select transistor to bias the chemically sensitive transistor, and the first terminal of the chemically-sensitive transistor directly coupled to a first terminal of a second row select transistor to couple the first terminal of the chemically-sensitive transistor to a column line, and
        a reference sensor including a reference transistor having a gate terminal coupled to a reference node, and a first terminal directly coupled to a third row select transistor to bias the reference transistor and directly coupled to a fourth row select transistor to couple the first terminal of the reference transistor to the column line, the reference transistor having a second terminal coupled to a second terminal of the second row select transistor; and
    a controller to apply a bias voltage to the reference node to place the reference transistor in a known state, acquire an output signal from the reference sensor in response to the applied bias voltage, and determine a defect associated with the array if the output signal does not correspond to the known state.

2. The apparatus of claim 1, wherein the bias voltage is sufficient to place the transistor in one of an on state or an off state.

3. The apparatus of claim 1, wherein the chemical sensor generates a sensor signal in response to a chemical reaction occurring within the reaction region.

4. The apparatus of claim 3, wherein the chemical reaction is a sequencing reaction.

5. The apparatus of claim 1, wherein the chemical sensor and the reference sensor share an access circuit coupled to the array, and the determination comprises determining that the shared access circuit is defective if the output signal does not correspond to the known state.

* * * * *